US006440139B2

(12) United States Patent
Michelson

(10) Patent No.: US 6,440,139 B2
(45) Date of Patent: *Aug. 27, 2002

(54) MILLING INSTRUMENTATION AND METHOD FOR PREPARING A SPACE BETWEEN ADJACENT VERTEBRAL BODIES

(76) Inventor: Gary K. Michelson, 438 Sherman Canal, Venice, CA (US) 90291

( * ) Notice: Subject to any disclaimer, the term of this patent is extended or adjusted under 35 U.S.C. 154(b) by 0 days.

This patent is subject to a terminal disclaimer.

(21) Appl. No.: 09/734,303

(22) Filed: Dec. 12, 2000

Related U.S. Application Data

(63) Continuation of application No. 08/688,758, filed on Jul. 31, 1996.

(51) Int. Cl.[7] ............................................... A61B 17/00
(52) U.S. Cl. ...................................................... 606/80
(58) Field of Search ............................. 606/80, 81, 82, 606/83, 97, 88

(56) References Cited

U.S. PATENT DOCUMENTS

| | | | |
|---|---|---|---|
| 5,356,414 A | 10/1994 | Cohen et al. | |
| 5,484,446 A | 1/1996 | Burke et al. | |
| 5,486,180 A | 1/1996 | Dietz et al. | |
| 5,489,307 A | 2/1996 | Kuslich | |
| 5,505,732 A | 4/1996 | Michelson | |
| 5,688,281 A | 11/1997 | Cripe et al. | |
| 5,910,143 A | 6/1999 | Cripe et al. | |

OTHER PUBLICATIONS

US 5,612,970, 03/1997, Houston et al. (withdrawn)

*Primary Examiner*—David O. Reip
*Assistant Examiner*—Tan-Uyen T. Ho
(74) *Attorney, Agent, or Firm*—Martin & Ferraro, LLP

(57) ABSTRACT

An apparatus and method for placing adjacent vertebrae at a fixed distance and angular relationship relative to each other, fixing said vertebrae in said position by use of a milling block engaging each of said adjacent vertebrae and then using a milling means, the depth, length and excursion of which from side to side are controlled by said apparatus to machine out a defined thickness of bone and a space of defined length, height, width and shape in preparation for receiving an interbody spinal implant or graft of known size and configuration are disclosed.

119 Claims, 23 Drawing Sheets

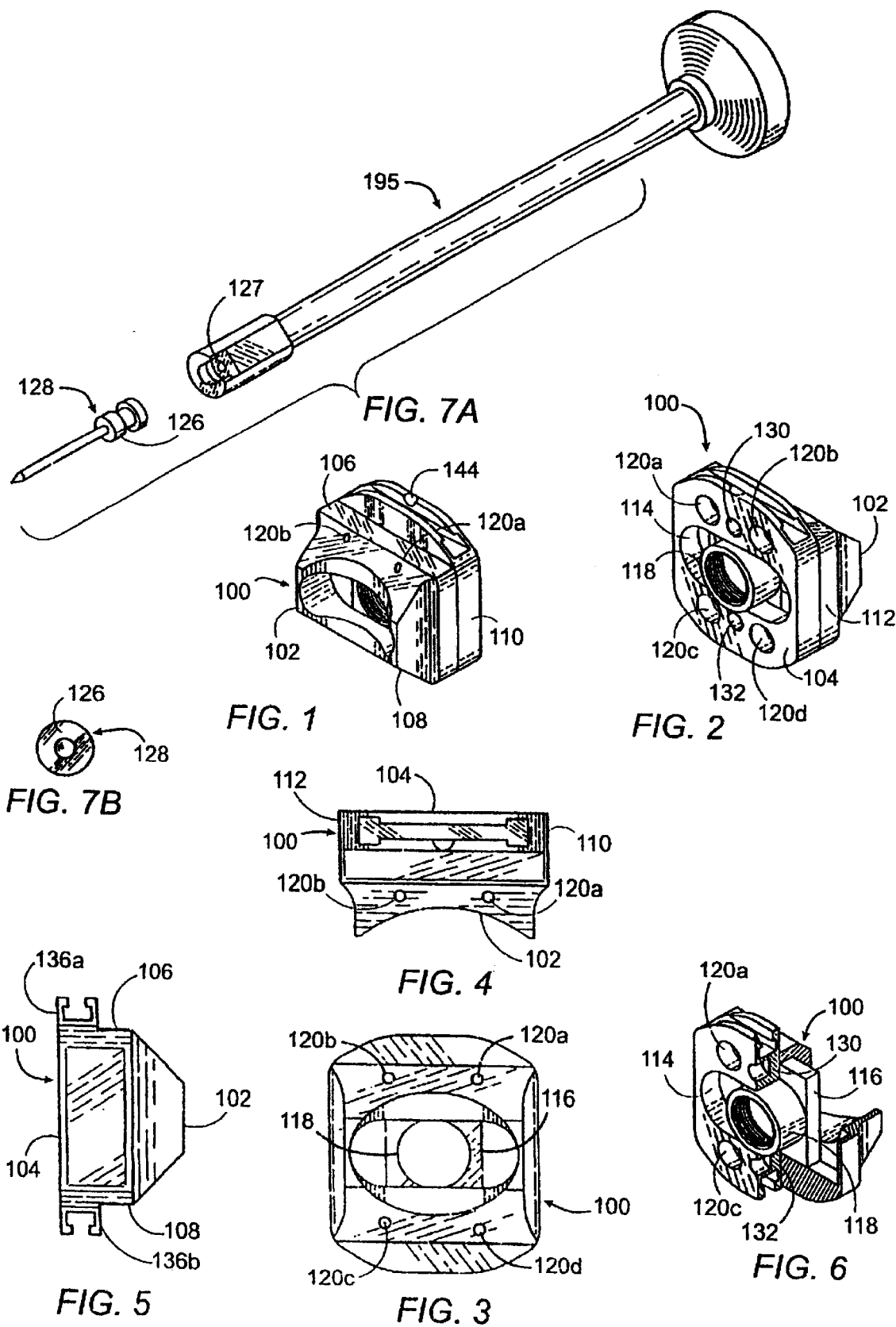

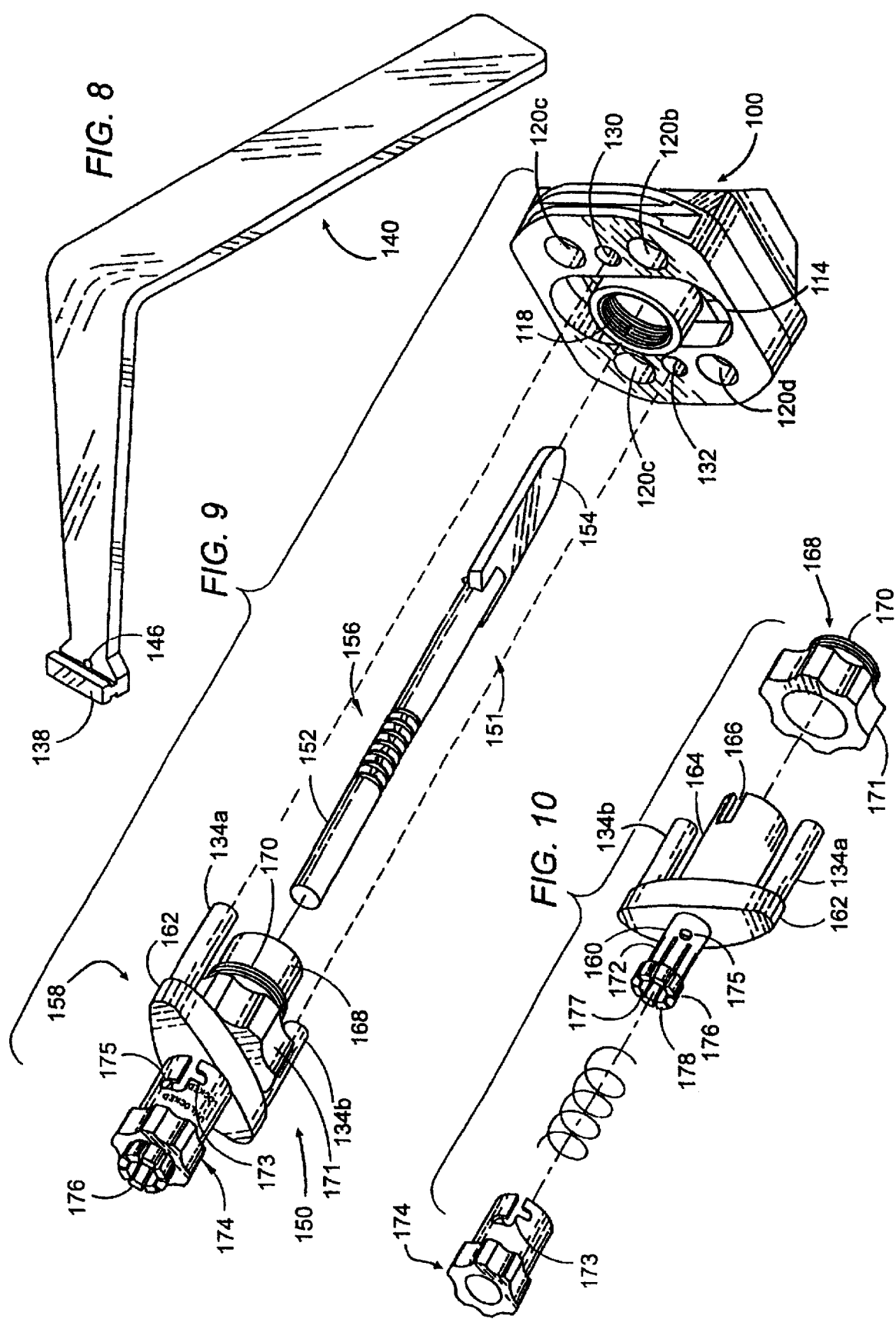

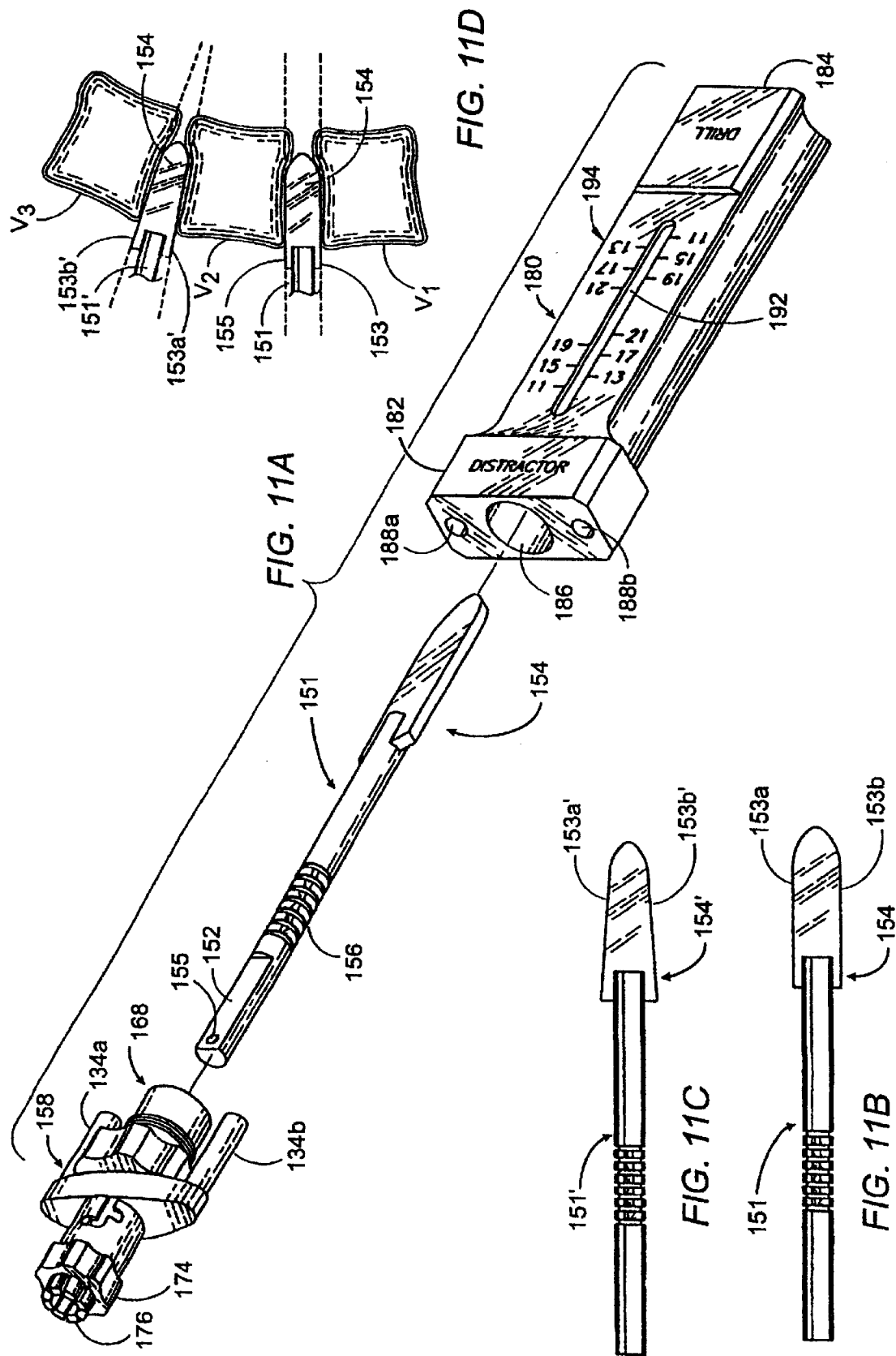

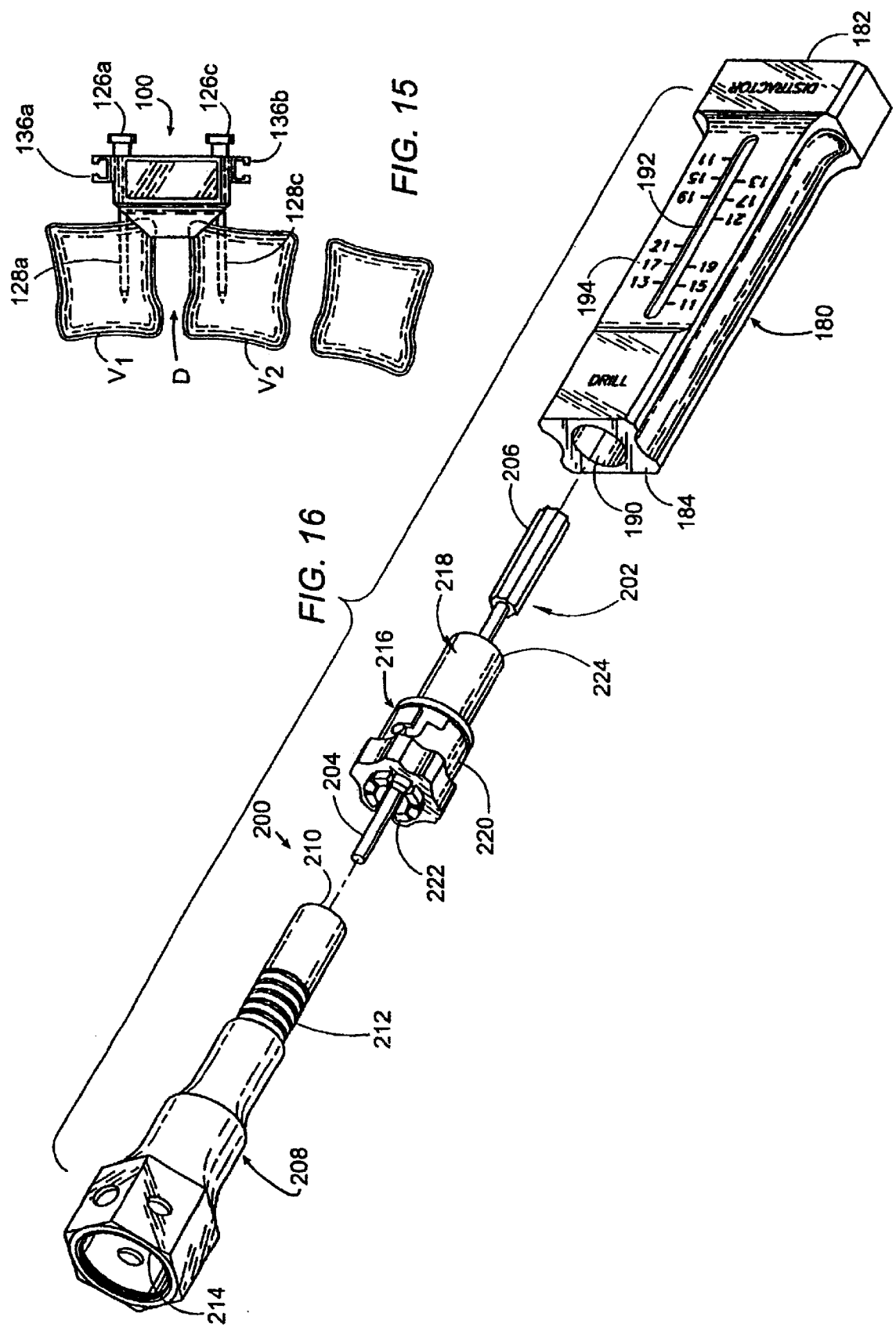

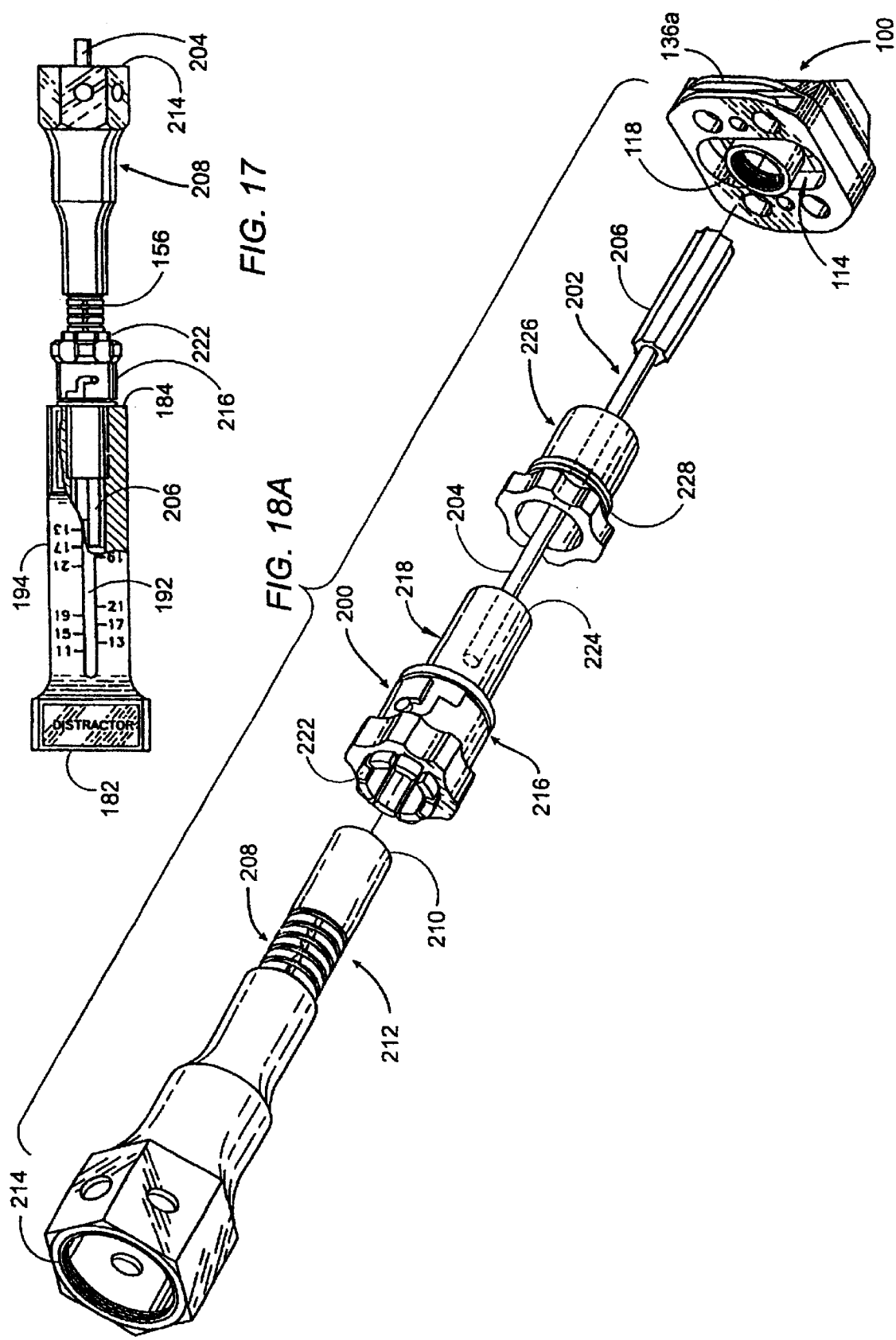

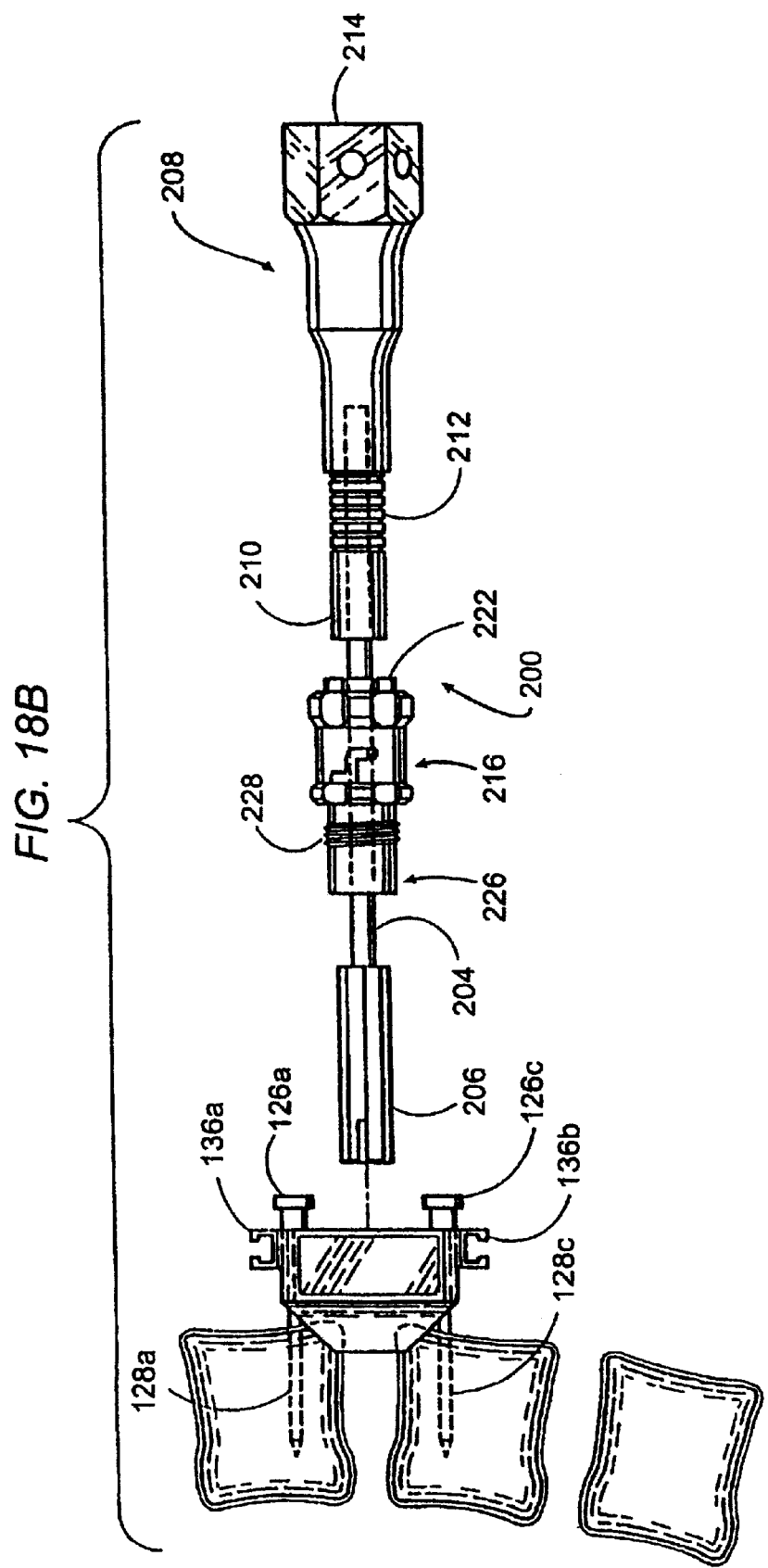

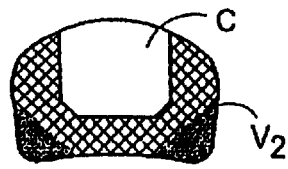
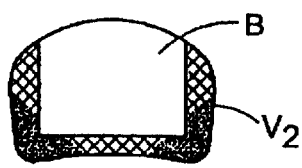
PRIOR ART
FIG. 26
FIG. 22
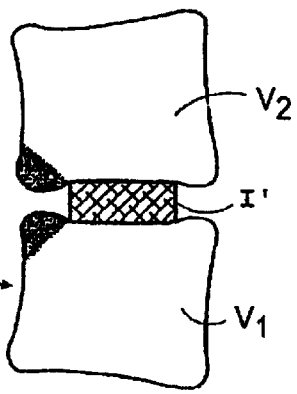
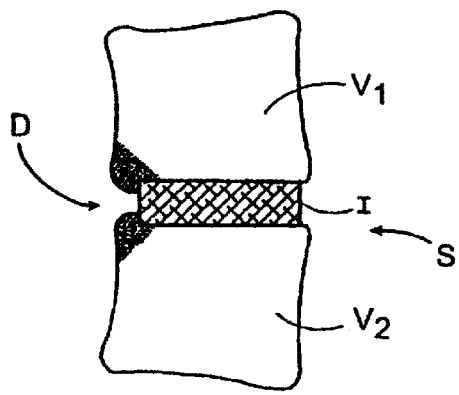
PRIOR ART
FIG. 24
FIG. 20
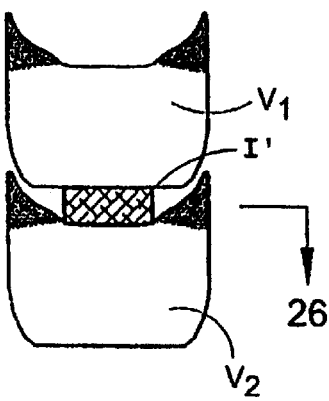
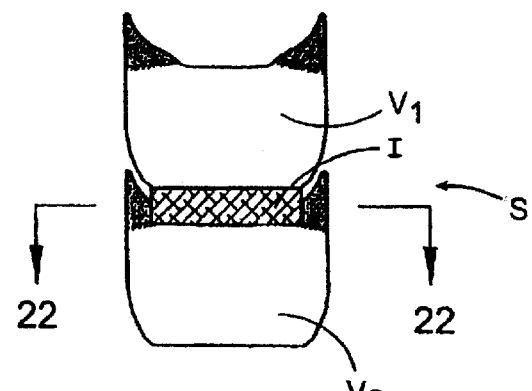
PRIOR ART
FIG. 25
FIG. 21
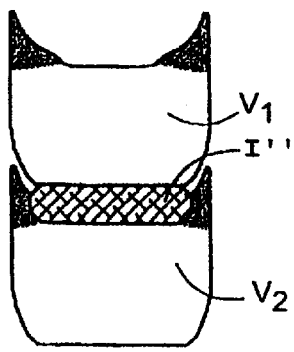
FIG. 23

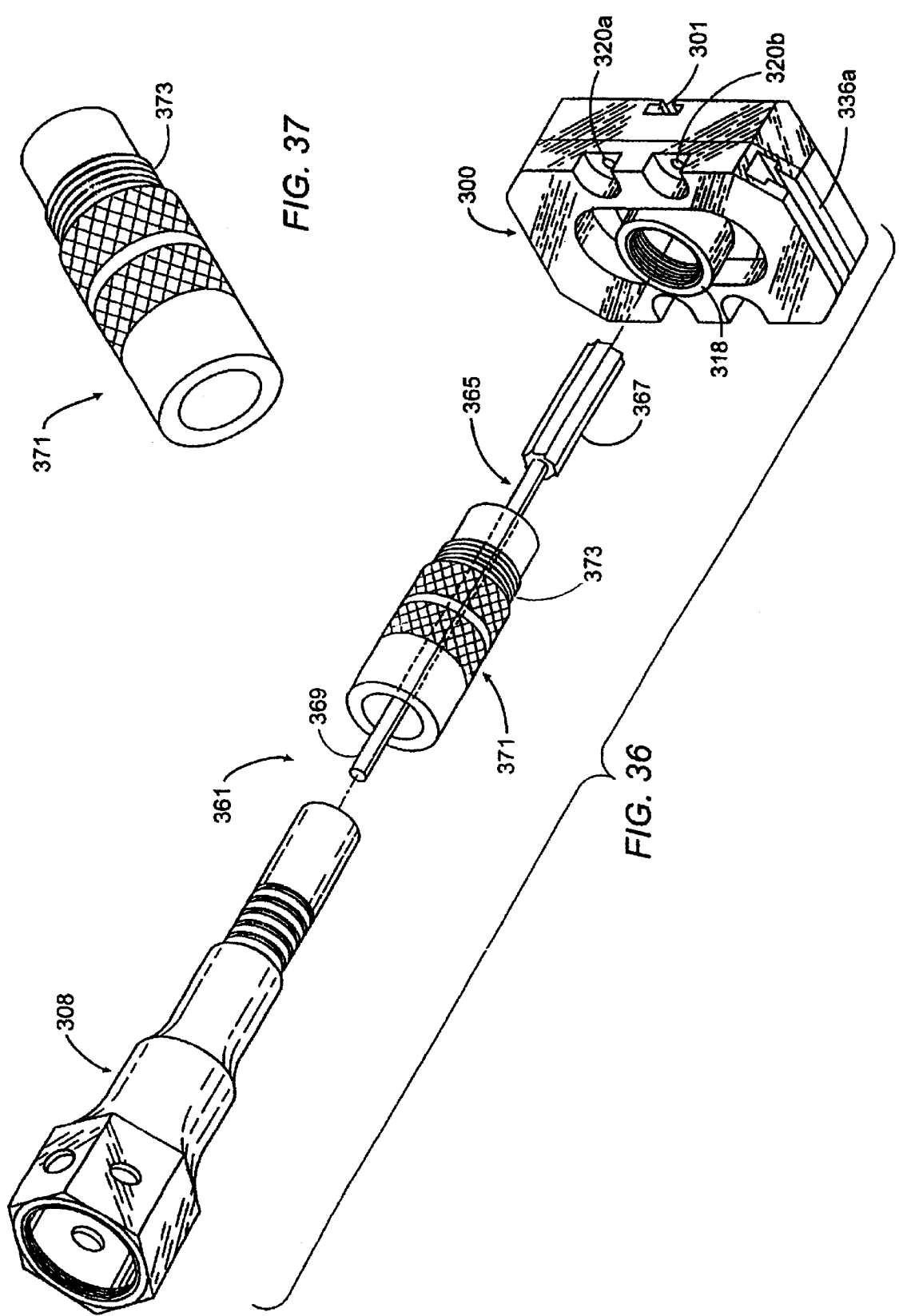

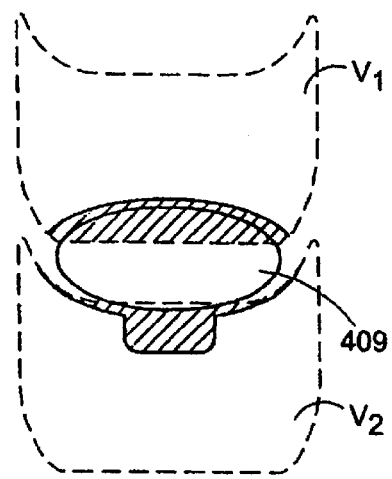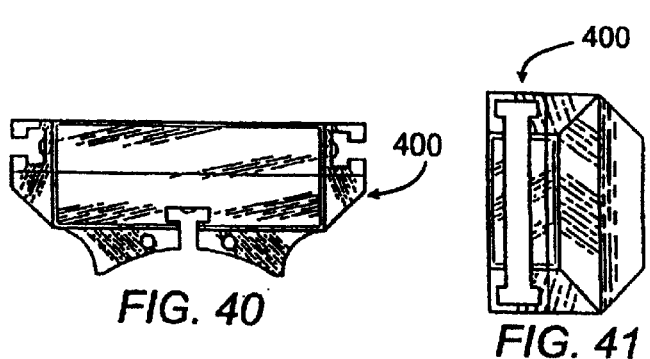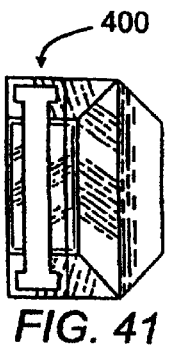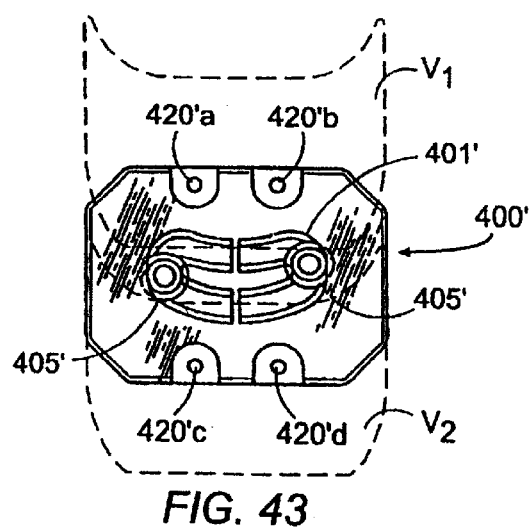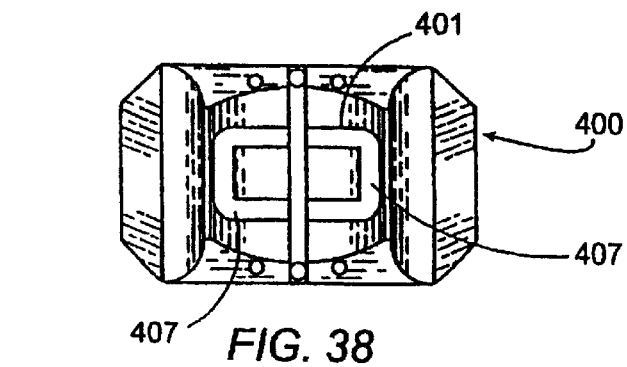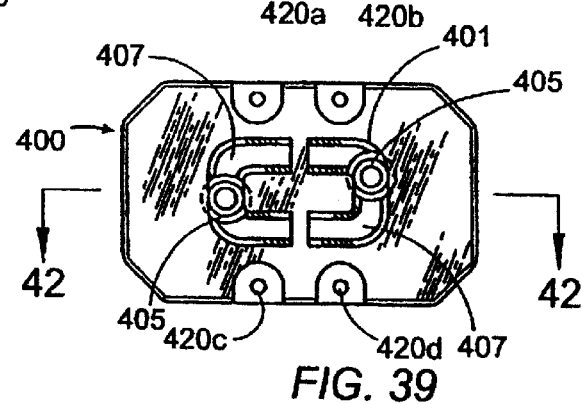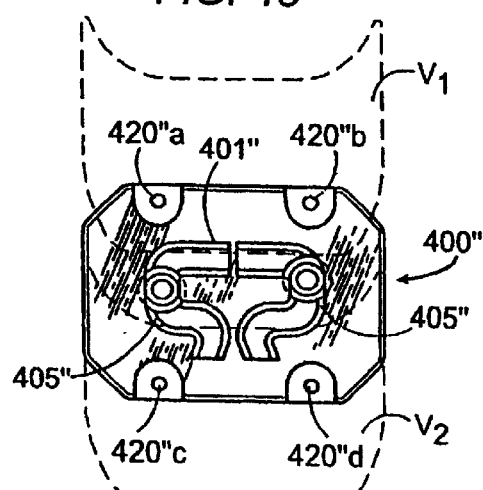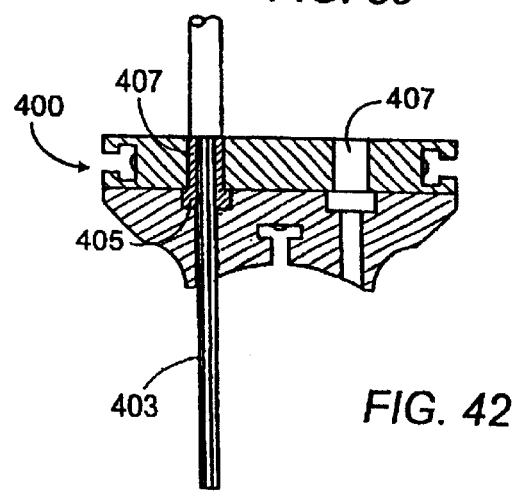

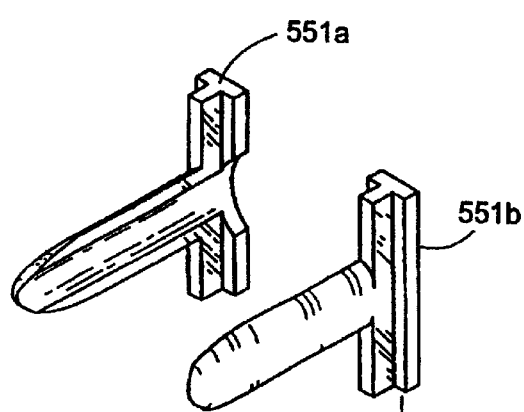
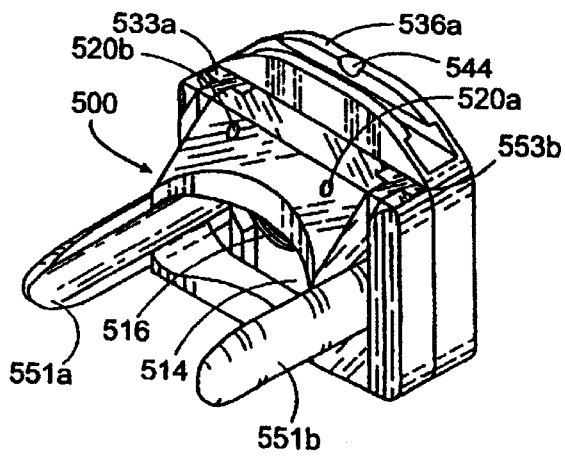
FIG. 46
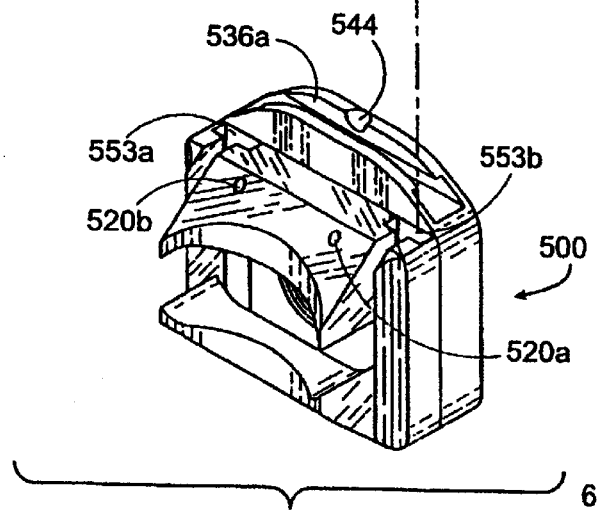
FIG. 47
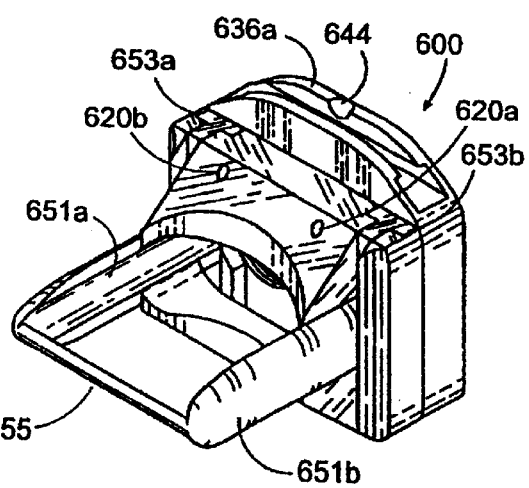
FIG. 48
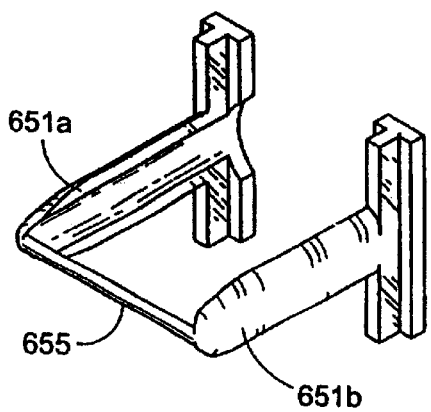
FIG. 49
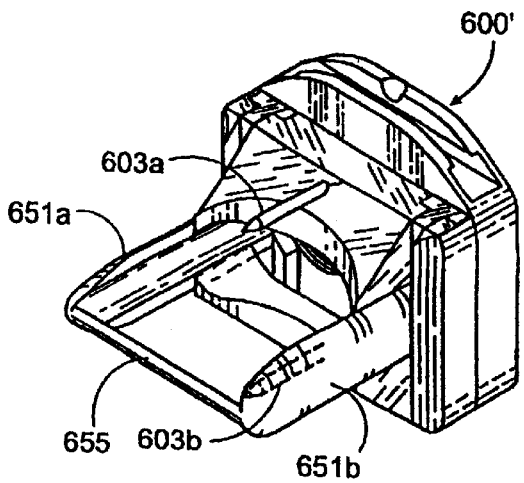
FIG. 50

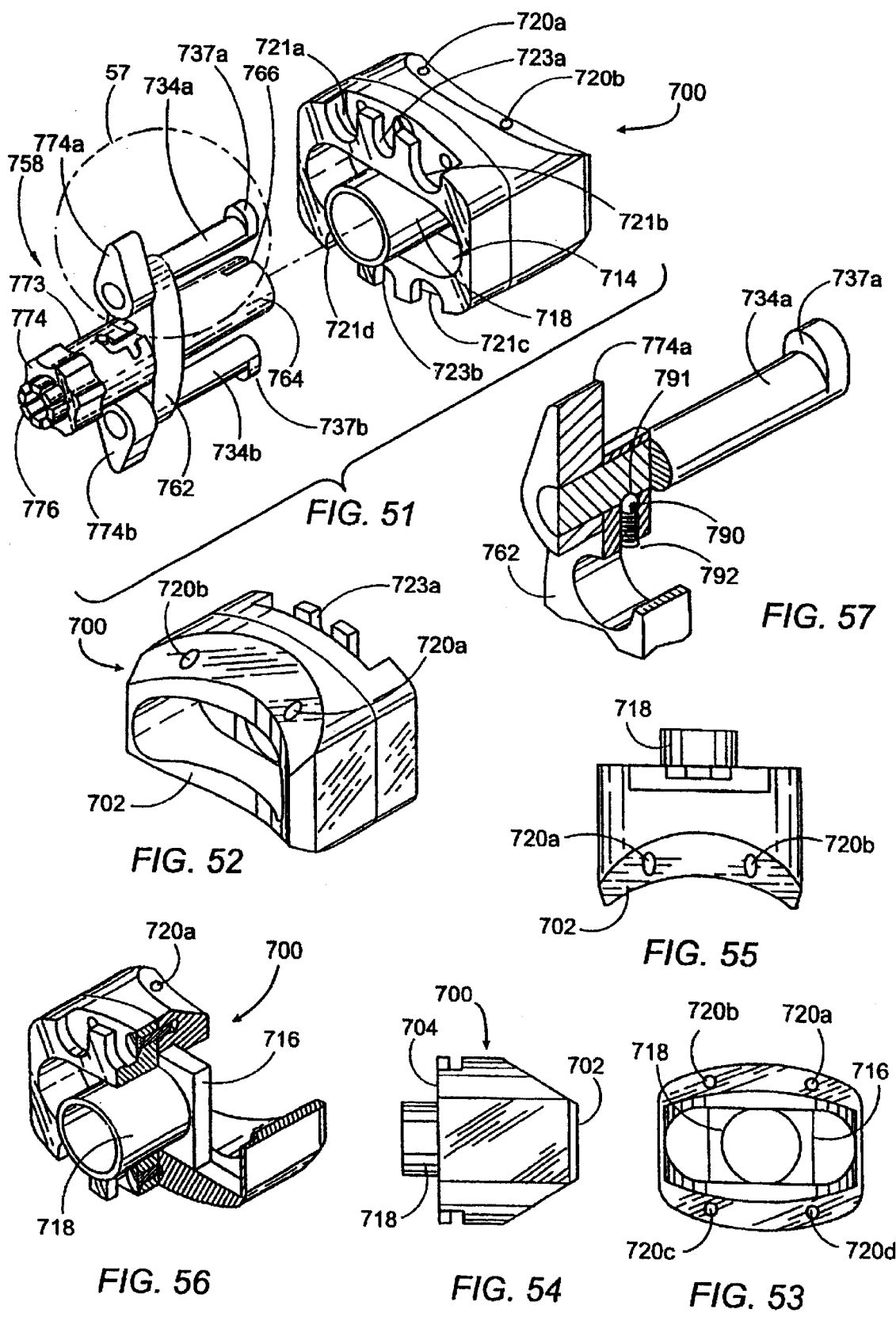

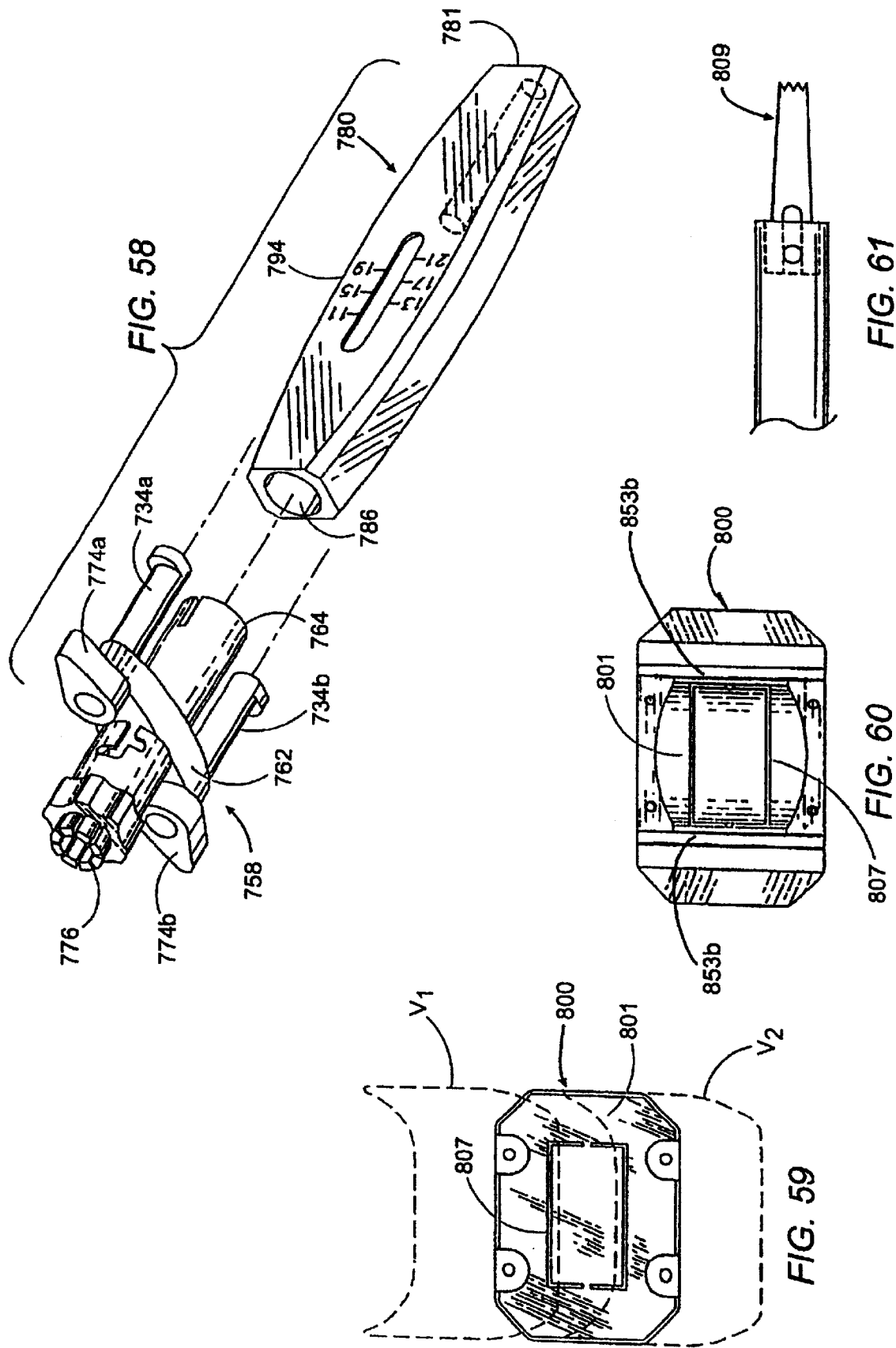

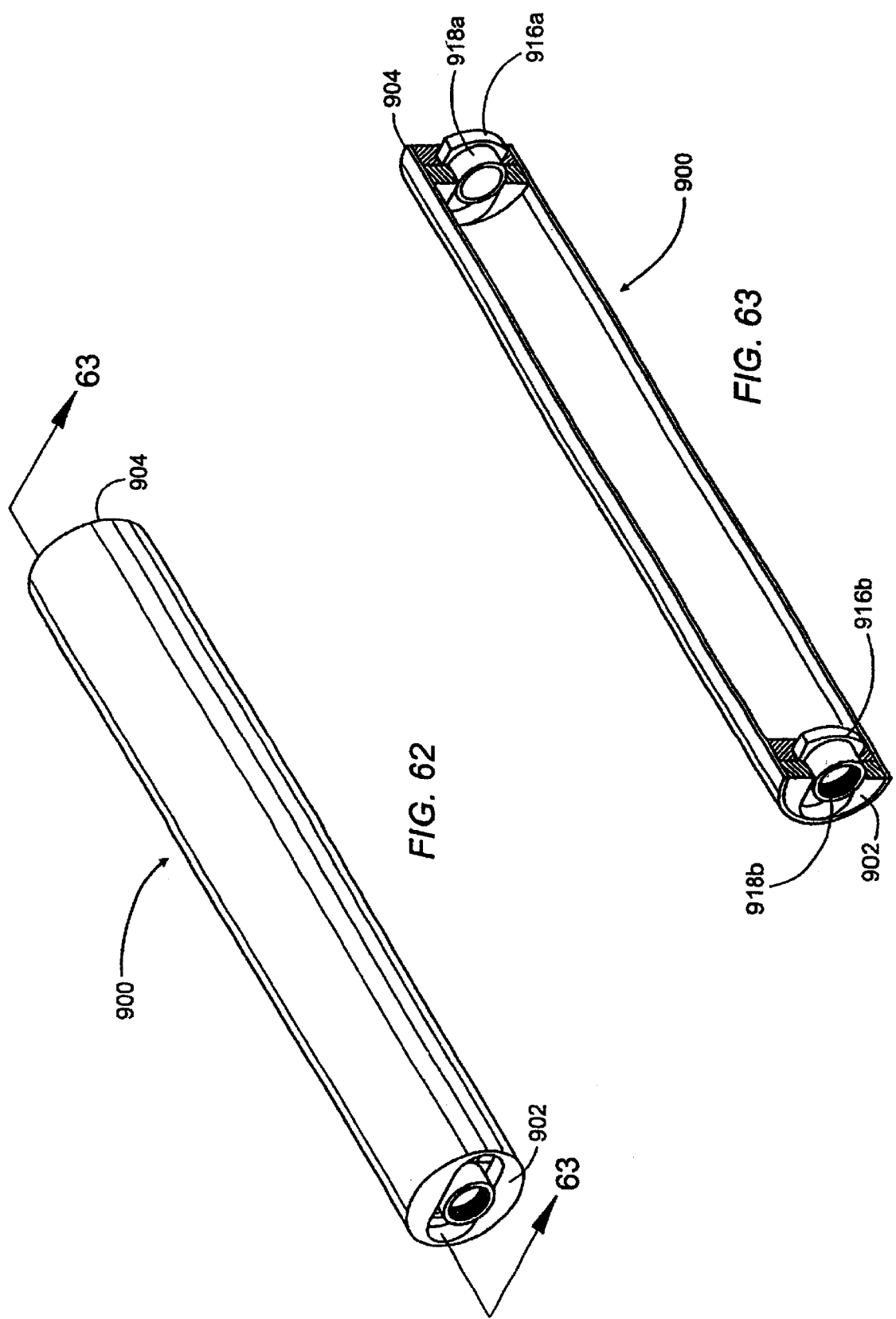

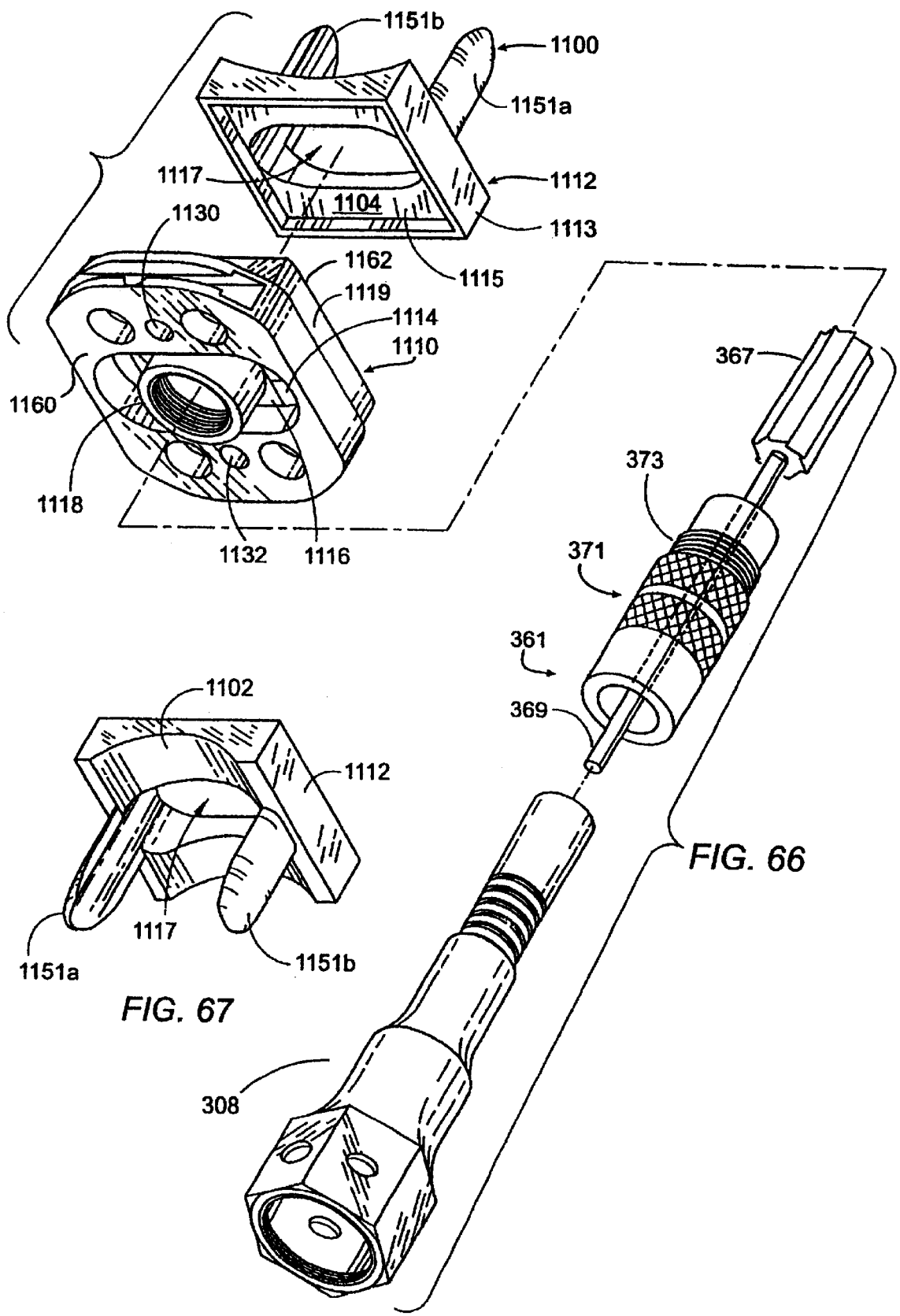

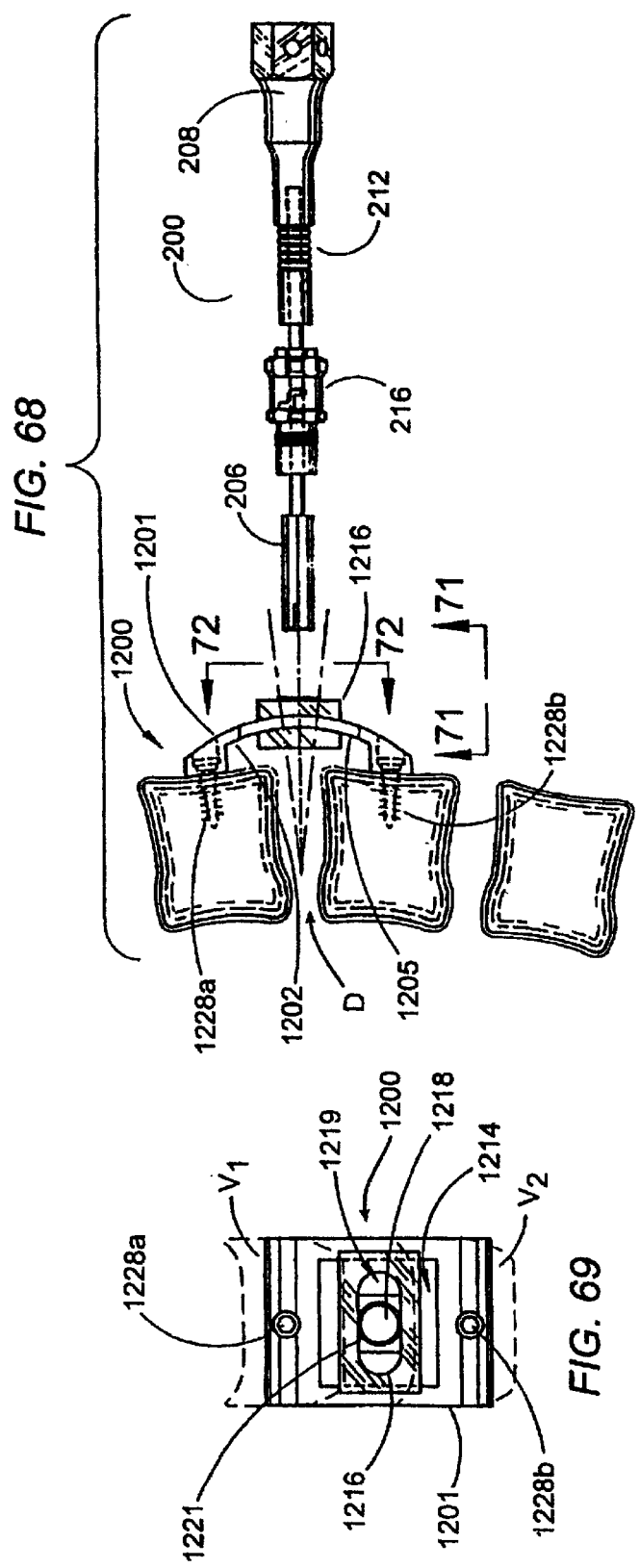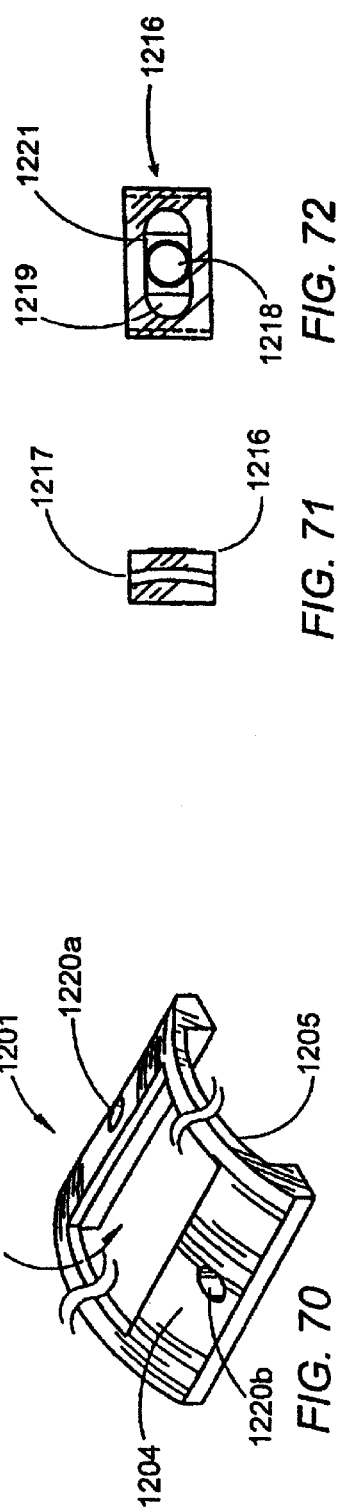

MILLING INSTRUMENTATION AND METHOD FOR PREPARING A SPACE BETWEEN ADJACENT VERTEBRAL BODIES

This is a continuation of application Ser. No. 08/688,758, filed Jul. 31, 1996, all of which is incorporated herein by reference.

BACKGROUND OF THE INVENTION

Spinal fusion is defined as the joining together of two or more adjacent vertebrae through a bridge of bone for the purpose of eliminating motion between those vertebrae. One specific type of spinal fusion is known to those skilled in the art as interbody fusion and consists of fusing the adjacent vertebrae through the disc space (the space previously occupied by the spinal disc interposed between the adjacent vertebral bodies). When such a procedure is performed from the anterior aspect of the spine (from the front) that procedure is known as anterior interbody fusion.

Typically, bone grafts are placed into the disc space to position the vertebrae apart so as to create more space for the nerves, to restore the angular relationship between said adjacent vertebrae to be fused, and to provide for material that can participate in and promote the fusion process. Substrates, other than bone, such as hydroxyapatite and/or artificial spinal fusion implants may also be used.

In general the ability to achieve bone fusion appears to be related to certain metabolic biochemical factors, the quality and quantity of the osteogenic material present (bone forming material, most commonly bone itself), the surface area available for the fusion to occur over, and the stability of the construct being fused (the ability to resist unwanted motion at the fusion site).

Consistent with the foregoing, it is desirable for the surgeon to place the largest fusion implant, generally bone, within the disc space as this provides for both the greatest surface area, and fusion mass. Furthermore, the greater the area of contact, the greater the stability of the bone-graft construct, such, that the graft is less likely to migrate, to itself collapse, or conversely to penetrate into the adjacent vertebrae as the forces across the fusion site are distributed over a greater area.

The disc space can best be described as having a biological rather than a geometric shape in that the adjacent vertebral endplate surfaces are complexly biconcave in portions, convex in others, while in still other areas extremely dense portions of bone project like "pillars" almost perpendicularly from the plane of the vertebral endplates, thereby forming partial, but substantial, side walls about the posterolateral (toward the back and side) portions of the disc space, the latter being particularly pronounced in the cervical spine.

As the bone graft used for the purpose of interbody fusion must have sufficient structural integrity to support the superincumbent body weight and the forces present across the portion of the body in which the graft is inserted, generally only quite solid portions of bone can be used for this purpose. Such portions of bone can only be cut, such as with a saw, rather than molded to fit the disc space. Even for the most skilled surgeon, it is not possible to shape such grafts to precisely fit the complex contours of the vertebral endplates adjacent the disc space. Therefore, the bone grafts are generally considerably smaller in width and depth than the disc space itself so as to confine such grafts to the more relatively flat area located about the mid portion of the vertebral endplates The term "relatively flat" is a correct description of the mid portion of the endplate in that even this region of the vertebral endplate is not truly flat, such that it is relatively rare to achieve full congruency between the machined surface of the bone graft and the biologically determined shape of the vertebral endplate. This further compromises the quality of the fusion construct in that the area of contact between the vertebrae and the graft is suboptimal with a loss of both support area and correspondingly, graft and construct stability.

Further factors tending to limit the dimensions of the graft to less than that of the disc space include, for example in the cervical spine, the danger of the graft accidentally escaping the disc space laterally (to the side), damaging the vertebral arteries and causing a cerebral infarct and the danger of penetrating posteriorly (toward the back) and injuring the spinal cord causing paralysis. Furthermore, the previously described pillars of dense bone projecting from the overall plane of the vertebral endplates in the posterolateral portions of the disc space and commonly known as either uncinate processes or the joints of Luschka, tend to block-the lateral and posterior placement of the graft(s) and tend to confine and limit the placement of the graft(s) to the anterior and central portions of the disc space.

To achieve fusion, it is necessary to at least vigorously scrape the outermost layer of the vertebral endplates until bleeding occurs to encourage the fusion, which invokes a healing process of the bone. Since the vertebral endplates are generally quite strong, it is desirable to preserve this structure even while scraping into it which can not reliably be achieved by the means of the prior art. In the past, anterior interbody fusion would be performed by removing at least a portion of the intervertebral disc and then utilizing hand held, free-hand instruments including, but not limited to, osteotomes, chisels, curettes, rongeurs, and burrs to scrape and shape the vertebral endplates and vertebral bone stock, which operations would be performed generally by working on one vertebra at a time, and independent of the position of the adjacent vertebra.

As a final consideration, not only are the vertebral endplates complexly shaped, but so are the interposed discs themselves. That is, the vertebrae of the spine are generally aligned in curved, rather than straight patterns when viewed from the side. When such curves are convex forward, as they are in the cervical and lumbar spine, the vertebrae are said to be in lordosis. Such lorcosis may be the result of wedging of the vertebral bodies, of the discs, or a combination of both. When lordosis is the result of a generally wedge shaped disc, it has generally proven difficult to reliably restore that overall wedged shape to the disc space itself for the purpose of fusing the adjacent vertebrae with precisely the correct amount of lordosis.

While the discussion above has been in regard to anterior interbody fusion, it may be desirable to replace a damaged or diseased disc with a flexible member, or mechanical "artificial disc", in which situation maximizing the surface area and congruency of contact, and controlling the angular and spatial relationships of the vertebrae adjacent that disc space would still be of great importance. As to be discussed, the present invention pertains to a means and method for the preparation of the space between adjacent vertebral bodies ("the disc space") suitable for the implantation of an artificial disc or for interbody spinal fusions.

Attempts have been made in the past to create a guided milling apparatus for use in surgery of such appendicular joints as that of the knee. For example, U.S. Pat. No. 5,486,180 issued to Dietz on Jan. 23, 1996 teaches the use of a guided milling apparatus. The Dietz apparatus is not capable of working in the spine to prepare a space between adjacent vertebral bodies and differs from the present invention in the following ways;

1) The Dietz apparatus requires that the bone be exposed end on (Col. 1, lines 34–36, Col. 2, lines 46–47, FIGS. 1,2, and 3). In the present invention, the "ends" of the vertebrae to be prepared are the vertebral endplates which can not be exposed on end except by dislocating the vertebrae which would cause the most grievous harm to the patient.
2) The Dietz apparatus is for the preparation of a single bone at a time (Col. 1, lines 34–36, Col. 1, lines 49–50; FIGS. 1,2,3,5,7).
3) The milling end of the Dietz apparatus removes the bone parallel to the template surface (Col. 4, lines 7–9, Col. 4, lines 50–53, FIGS. 5 and 7). In the spine, there is insufficient space available within the disc space interposed between adjacent vertebrae to insert, accommodate or operate the Dietz mechanism; this would be true regardless of actual size of the Dietz device for any size that would remain workable for use in the spine.
4) The Dietz apparatus in incapable of affixing the opposed bones on both sides of the joint simultaneously, or of preparing both joint surfaces with the opposed bones in fixed relationship with each other.
5) The Dietz apparatus teaches a means for cutting across two dimensions while controlling (fixing) for depth. (FIGS. 5, 27).
6) Dietz teaches that the mill end is too large to pass through the template guide surface so as to confine the mill end beneath the guide means. (Col. 3, lines 8–19, Col. 4, lines 24–53; FIGS. 5 and 7). This thus requires that the enlarged burr portion enters the bone not through its end or face, but rather on the front surface of the bone, which entrance occurs through a cut out slot, is deep to the guide plate, and with the burr spinning about an axis parallel to the longitudinal axis of the bone itself. (Col. 2 Line, 35–37, FIGS. 1 and 2).
7) The Dietz apparatus is limited to the cutting by use of a burr along a nonlinear path. (Col. 2, lines 65; Col. 3, lines 4–6; Col. 4, line 2, FIGS. 4 and 6). This is not arbitrary as the path of the burr is guided by either or both of a pivot, allowing only for a series of arcs, and/or a branched and serpentine slot system also configured to produce only a series of arcs. (Col. 2, lines 41–42, line 52, line 65 through Col. 3, line 4, and FIGS. 1, 2, 4 and 26).

There is therefore a need for a method and means for preparing the vertebral bodies and the vertebral endplates adjacent to a disc space to be fused by interbody fusion that.

1) allows for the safe preparation of the disc space to the optimal depth and width so as to allow for the correct use of the largest possible fusion implant which would be associated with the direct benefits of providing for the maximum mass of osteogenic material, the largest possible surface area for fusion to occur over, increased graft and construct stability secondary to the increased area of contact, and the greatest protection against implant collapse or penetration into the vertebral bodies from the distribution of the loads over the greatest surface area;
2) allows for the preparation of the vertebral endplates to a known and uniform surface configuration, which configuration can be matched by a corresponding surface of the fusion implant: thereby providing for the greatest possible interface congruity between the vertebral endplates and fusion implant, and providing for the optimal contact surface, enhanced fusion area, enhanced graft and construct stability, and decreased load per surface area;
3) allows for the restoration of the correct vertebral alignment by preparing the vertebral endplates in fixed relationship-to each other adjacent the disc space so as to three dimensionally shape the disc space-fusion implant site;
4) allows for an efficient and reliable means for scraping the central portions of the outer layer of the vertebral endplates without the danger of removing those structures entirely; and
5) allows for the extension of the fusion area into the extremely supportive and extremely dense bone of the posterior lateral regions of the disc space.

SUMMARY OF THE INVENTION

The present invention is directed to an apparatus and method for use in spinal surgery for creating a space of selected shape and dimensions across the disc space between two adjacent vertebrae of the spine. The present invention comprises an integrated system of instrumentation and a surgical method that is capable of placing the adjacent vertebrae to be operated upon in proper angular relationship to each other, of locking the vertebrae in that position, of simultaneously preparing both vertebral endplates for the procedure, be it fusion or disc replacement, and specifically the creation of a space of a known shape and dimensions. The foregoing is achieved by the use of a power milling apparatus such that all free hand motions are eliminated and the site size, shape, and configuration, as well as the extent of vertebral endplate resection are made predictable, precise and reproducible. The instrumentation of the present invention allows for the safe controlled and protected preparation of the disc space to the optimal depth and width. The present invention allows for implant(s) or bone grafts to be placed onto the area of dense bone at the posterior lateral aspects of the disc space. The present invention allows for the maximum stability of the graft/implant, as well as the construct, by providing for the greatest possible interface surface area and congruency between the graft/implant and each of the adjacent vertebrae.

The present invention further provides for increased stability by creating butted corners, posterolaterally, into which the graft/implant may be fitted which corners prevent further movement of the graft/implant either posteriorly or to either side of the created space. The present invention is capable of the uniform preparation (scraping) of the central portion of the vertebral endplate otherwise leaving that structure intact, if so desired. The present invention makes possible the preparation of the disc space to be prepared in anatomical angular conformation, and the disc space can be formed so as to correspond to the known shape of the graft/implant to be utilized.

In one embodiment, the apparatus of the present invention comprises a milling block having a front face configured for placement against a segment of the spine and having at least one aperture for accessing each of the two vertebral endplates of the vertebral adjacent the disc space. The adjacent vertebrae are placed in the appropriate spatial relationship to each other with a distractor means. Instrumentation is disclosed for selecting and calibrating the maximum safe penetration depth of the distractor means into the disc space and for locking the selected depth to prevent unwanted over penetration into the disc space. The distractor means may be part of the milling block or may be a separate member that is coupled to the milling block either directly or by a distractor holder.

Associated with the milling block is a bone removal means for removing a portion of bone from each of the vertebral endplates adjacent the disc space. The bone removal means is capable of accessing the vertebral endplates through the aperture in the milling block. The milling block is held firmly against a segment of the spine by securing means, such as prongs, pins, screws and the like, or by the distractor means itself inserted into the disc space in contact with the endplates of the adjacent vertebrae Instrumentation is disclosed for selecting, calibrating and limiting the penetration depth of the bone removal means into the disc space and/or vertebrae and to prevent unwanted over penetration into the disc apace and/or vertebrae. The bone removal means may be guided with an instrument guiding means located in the aperture of the milling block and in slideable relation to the milling block permitting slideable transverse motion and/or vertical motion during operation of the bone removal means to remove a portion of bone from the vertebral endplates adjacent to the disc space.

The following is a brief outline of the steps of the surgical method of the present invention describing the use of the specific instrumentation in regard to the preferred embodiment:

1. The area of the spine to be fused is exposed and a partial disectomy is performed, whereby a portion and preferably a large portion of the disc is removed while preserving the annulus fibrosis portion of the disc along at least both sides of the disc space.
2. The interspace so created is distracted and while not requisite, preferably to its optimal height, which height is determined by the known normal spatial relationships for that area the adjacent soft tissue structures. The interspace is then measured for height, depth, and width. The width of the interspace may be determined in reference to the inferior portion of the vertebral endplate of the superior vertebrae, and this determines the selection of the appropriate width for the milling block. The measured depth of the interspace, that is the distance between the front and back of vertebrae, will determine the selection of a distractor and milling means of slightly lesser depth. The height and depth of the interspace will determine the selection of the appropriate height and length of the distractor element, the shape of which is determined by both the need to either maintain or restore lordosis, as well as the shape of the implant which may or may not be wedged.
3. The correct distractor element is selected, having either a known fixed length, or preferably is adjustable and its optimal fixed length adjusted using a calibration gauge, integral markings or similar means.
4. The distractor apparatus is then attached to the milling block which has already been selected for the correct width.
5. The combined distractor apparatus and milling block assembly is then brought to the fusion site and the distractor element is introduced into the disc space. The distractor element may be introduced into the disc space turned on its side so as to facilitate introduction and then turned 90 degrees to distract the space or the distractor element may be introduced perpendicular to the plane of the disc space relying on its bullet-shaped leading edge portion to distract the vertebrae apart. The angular relationship of the two vertebral bodies adjacent that disc space will then be determined by the shape of the distractor element. It is appreciated that while not preferred, a distractor could be inserted into the disc space first, then the milling block assembly is brought into place relative to the spine thereafter.
6. The milling block is then secured to the anterior aspect of the spine preferably, by engaging each of the adjacent vertebrae.
7. The width and depth of bone resection may then be easily confirmed visually prior to any actual bone resection.
8. The distractor element and distractor apparatus are removed from the disc space.
9. The proper dimensioned bone removal means, corresponding to the previously employed distractor element, is selected and using the receiving depth gauge, the bone removal means is adjusted for depth and locked.
10. The bone removal means is secured to the milling port of the milling block, and the space is then milled to remove a portion of bone from the endplates adjacent to the disc space.
11. The milling apparatus is removed and the prepared space may be irrigated and sectioned through the milling block, or alternatively the entire milling assembly including the milling block may first be removed and the prepared space then irrigated and sectioned.
12. The prepared space is distracted utilizing conventional means and the appropriate implant or implants are then inserted into the prepared space.

In the alternative, the surgical method of the present invention may be performed by utilizing a separable milling block having a separable member with bilateral, lateral distractor elements such that the distractor elements are left in place in the disc space while steps 9–12 above of the method are performed. However, in this instance no distraction would be necessary in step 12 as the distractor elements remain in place while the appropriate implant(s) are inserted into the prepared space and the distractor elements are subsequently removed. The placement of bilateral distractor elements also provides a safety means for preventing the bone removal means and implant from exiting from the sides of the: disc space and out of the spine.

OBJECTS OF THE PRESENT INVENTION

It is an object of the present invention to provide for a surgical method and instrument means for performing interbody spinal fusion or in the alternative of inserting an "artificial disc implant" for the purpose of maximizing the width and optimizing the depth of the disc and the bone removed from front to back, or back to front, from the vertebral endplates adjacent the disc space to be fused or implanted while confining such bone resection safely within the lateral, anterior (front) and posterior (back) limits of the disc space.

It is another object of the present invention to provide for a surgical method and instrument means for performing interbody spinal fusion or "artificial disc", implantation that provides for the rapid creation of both a known surface contour of each of the vertebral endplates adjacent a disc space as well as a known and reproducible shape of the fusion or implantation site itself.

It is another object of the present invention to provide for a surgical method and instrument means for performing interbody spinal fusion that allows for the utilization of a larger interbody spinal fusion implant(s) than was possible with the prior art, such an implant having the capacity for providing increased amounts of osteogenic material, increased surface area, increased area of contact, increased stability and the ability to provide for greater support through the fusion area.

It is another object of the present invention to provide for a surgical method and instrumentation for performing the preparation of the space between adjacent vertebrae for the purpose of implanting an artificial disc or fusion implant(s) having the optimal cross sectional area of contact with said adjacent vertebrae and where said cross sectional area may be as large as possible while remaining safely within the perimeter of the endplates of the adjacent vertebrae.

These and other objects of the present invention will become apparent from a review of the accompanying drawings and the detailed description of the drawings.

BRIEF DESCRIPTION OF THE DRAWINGS

FIG. 1 is a front perspective view of the milling block of the present invention.

FIG. 2 is a rear perspective view of the milling block of the present invention.

FIG. 3 is a front elevation view of the milling block of the present invention.

FIG. 4 is a top plan view of the milling block of the present invention.

FIG. 5 is a side elevational view of the milling block of the present invention.

FIG. 6 is a partial sectional view of the milling block of the present invention showing the sliding instrument guide within the milling block.

FIG. 7A is a side perspective view of a pin driving instrument and a pin used to secure the milling block of the present invention to a segment of the spine.

FIG. 7B is a top plan view of a pin used to secure the milling block of the present invention to the vertebrae.

FIG. 8 is a front perspective view of a handle used to hold the milling block of the present invention.

FIG. 9 is an exploded view of a distractor and distractor holder of the present invention with the distractor shown about to be inserted into the milling block of the present invention.

FIG. 10 is an exploded perspective view of the distractor holder of the present invention.

FIG. 11A is an exploded view of the distractor holder, the distractor and the calibration gauge of the present invention.

FIG. 11B is a side elevational view of the distractor of the present invention having a insertion end for placing two adjacent vertebrae in parallel relationship to each other.

FIG. 11C is a side elevational view of the distractor of the present invention having a converging insertion end for placing two adjacent vertebrae in angular relationship to each other such as lordosis.

FIG. 11D is a side elevational view of a segment of the spine with two distractors of the present invention placed at two adjacent disc levels illustrating the creation of lordosis with one distractor and the parallel spacing of the vertebrae by the other distractor.

FIG. 15 is a side elevational view of a segment of the spine with the milling block of the present invention engaged to two adjacent vertebrae by a plurality of pins shown partially in hidden line.

FIG. 16 is an exploded perspective view of the bone removal assembly and calibration gauge of the present invention.

FIG. 17 is a partial cut-away of a front elevational view of the calibration gauge of the present invention with the bone removal assembly inserted therein to adjust the depth of the milling bit.

FIG. 18A is an exploded perspective view of the bone removal assembly of the present invention about to be inserted into the milling block of the present invention.

FIG. 18B is an exploded side elevational view of the bone removal assembly being inserted into the milling block of the present invention shown engaged to a segment of the spinal column.

FIG. 20 is a side elevational view of a segment of the spinal column having an implant inserted in the space created across the disc space and into the adjacent vertebrae with the milling block instrumentation and method of the present invention.

FIG. 21 is a front elevational view of a segment of the spine having an implant with flat side walls from top to bottom inserted in the space created across the disc space and into the adjacent vertebrae with the milling block instrumentation and method of the present invention.

FIG. 22 is a sectional view of a vertebra taken along line 22—22 of FIG. 21 illustrating the space created into the vertebrae by the milling block instrumentation and method of the present invention.

FIG. 23 is a front elevational view of a segment of the spinal column having an implant with curved side walls from top to bottom inserted into the space created across the disc space and into the adjacent vertebrae by the milling block and instrumentation of the present invention.

FIG. 24 is a side elevational view of a segment of the spinal column showing an implant inserted between two adjacent vertebrae with the methods and instrumentation of the prior art.

FIG. 25 is a front elevational view an implant inserted between two adjacent vertebrae with the methods and instrumentation of the prior art.

FIG. 26 is a sectional view along lines 26—26 of FIG. 25 illustrating the space created in the vertebrae by the methods and instrumentation of the prior art.

FIG. 36 is an exploded perspective view of an alternative embodiment of the bone removal assembly and the milling block of the present invention shown in FIG. 27.

FIG. 37 is a perspective view of the adapter sleeve of the bone removal assembly of the present invention shown in FIG. 36.

FIG. 38 is a front elevational view of an alternative embodiment of the milling block of the present invention.

FIG. 39 is a rear elevational view of the alternative embodiment of the milling block of the present invention shown in FIG. 38.

FIG. 40 is a top plan view of the alternative embodiment of the milling block of the present invention shown in FIG. 38.

FIG. 41 is a side elevational view of the alternative embodiment of the milling block of the present invention shown in FIG. 38.

FIG. 42 is a sectional view along lines 42—42 of FIG. 39 of the milling block of the present invention having a bone removal member inserted therein for milling a space between two adjacent vertebrae.

FIG. 43 is a rear elevational view of an alternative embodiment of the milling block of the present invention with two adjacent vertebrae shown in hidden line.

FIG. 44 is a rear elevational view of an alternative embodiment of the milling block of the present invention with two adjacent vertebrae shown in hidden line.

FIG. 45 is a anterior elevational view of a segment of the spinal column illustrating the space created with the milling block of FIG. 44 and an artificial disc implanted within the created space.

FIG. 46 is a front perspective view of an alternative embodiment of the milling block of the present invention with a pair of distractor elements in place.

FIG. 47 is a front perspective exploded view of the alternative embodiment of the milling block of FIG. 46 and a pair of distractor elements of the present invention.

FIG. 48 is a front perspective view of an alternative embodiment of the milling block of the present invention.

FIG. 49 is a side perspective view of a pair of distractor elements of the present invention shown joined together at their tips.

FIG. 50 is a front perspective view of al alternative embodiment of the milling block of the present invention.

FIG. 51 is an exploded rear perspective view of an the preferred embodiment of the milling block and distractor holder of the present invention for use in the cervical spine.

FIG. 52 is a front perspective view of the embodiment of the milling block shown in FIG. 51.

FIG. 53 is a front elevational view of the embodiment of the milling block shown in FIG. 51.

FIG. 54 is a side elevational of the embodiment of the milling block shown in FIG. 51.

FIG. 55 is a top plan view of the embodiment of the milling block shown in FIG. 51.

FIG. 56 is a rear perspective fragmentary view of the embodiment of the milling block shown in FIG. 51.

FIG. 57 is a fragmentary view of the distractor holder. along line 57 of FIG. 51.

FIG. 58 is a side perspective view of an embodiment of a combined calibration gauge and handle of the present invention.

FIG. 59 is a rear elevational view of an alternative embodiment of the milling block of the present invention with two adjacent vertebrae shown in hidden line.

FIG. 60 is a front elevational view of the alternative embodiment of the milling block shown in FIG. 59.

FIG. 61 is a side elevational view of a cutting instrument for use with the alternative embodiment of the milling block apparatus shown in FIG. 59.

FIG. 62 is a side perspective view of an alternative embodiment of the milling block apparatus of the present invention.

FIG. 63 is a sectional view along line 63—63 of FIG. 62 of the milling block apparatus of the present invention.

FIG. 66 is an exploded rear perspective view of an alternative embodiment of the milling block and bone removal assembly of the present invention.

FIG. 67 is a front perspective view of the distractor portion of the milling block of FIG. 66.

FIG. 68 is a side elevational view of an alternative embodiment of the milling block and bone removal assembly of the present invention shown engaging two adjacent vertebrae.

FIG. 69 is a rear elevational view of the milling block of FIG. 68.

FIG. 70 is a rear perspective view of the milling block of FIG. 68.

FIG. 71 is an elevational view along lines 71–71 of FIG. 68.

FIG. 72 is an elevational view along lines 72—72 of FIG. 68.

DETAILED DESCRIPTION OF THE DRAWINGS

Figure 12:
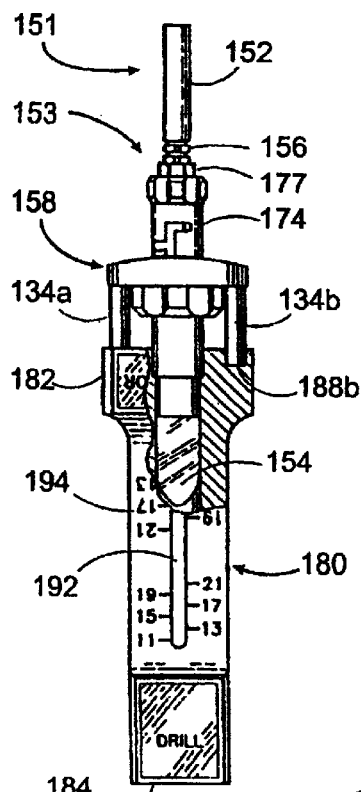
FIG. 12 is a partial cut away of a front elevational view of the calibration gauge of the present invention with the distractor inserted therein and the distractor holder coupled to the distractor insertion end of the calibration gauge.

Referring to FIGS. 1–66, the instrumentation of the present invention comprises a milling block, generally referred to by the numeral 100. The milling block 100 has an overall generally rectangular configuration having a front face 102, an opposite rear face 104, a top side 106, a bottom side 108 and left and right sides 110 and 112, respectively. The front face 102 comprises a surface having a concave configuration that conforms to the natural curvature of the anterior aspect of a segment of the human spinal column and permits the placement of the milling block 100 in close proximity to the anterior aspect of the spinal column. The milling block 100 comprises a central aperture 114 through the center of the milling block 100. The aperture 114 is preferably oblong-shaped, having an approximate width of 18–30 mm for use in the cervical spine, 30–50 mm for use in the lumbar spine, and if the milling, block 100 is used on the left and right sides of the mid sagittal axis of a lumbar vertebrae separately, the approximate width of the aperture 114 is 15–25 mm and the approximate height of the aperture 114 is 5–20 mm. Located within the aperture 114 is a sliding mill guide 116 having a threaded port 118 for engaging various instrumentation as discussed in detail below. The mill guide 116 slides in a transverse motion from side to side within the central aperture 114 along the transverse axis of the aperture 114.

The milling block 100 comprises a plurality of pin holes 120*a*–*d* which pass through the milling block 100 from the rear face 104 through the front face 102. The pin holes 120*a*–*d* have a wider diameter entrance at the rear face 104 of the milling block 100 and have a narrower diameter passage at the front face 102 of the milling block 100. The wide diameter entrance of the pin holes 120*a*–*d* permit the countersinking of the head portion 126 of pin 128 illustrated in FIGS. 7A and 7B and described in detail below.

The rear face 104 of the milling block 100 includes blind holes 130 and 132 centrally positioned and located between the pin holes 120*a*–*b* and 120*c*–*d*, respectively. The blind holes 130 and 132 receive posts 134*a* and 134*b* of the distractor holder 158 illustrated in FIG. 9 and described in detail below. The top and bottom sides 106 and 108 of the milling block 100 comprise tracks 136*a* and 136*b* having an inverted T-shaped configuration for engaging a T-shaped rail member 138 of the handles 140 and 142 illustrated in FIG. 8 and described in detail below. Each of the tracks 136*a* and 136*b* have a depression 144 for engaging a detent means 146 on the handles 140 and 142 for centering the handles 140 and 142 relative to the milling block 100 and for locking the handles 140' and 142 in place once they are attached to the milling block 100.

Referring to FIG. 8, the handle 140 is shown having a general L-shaped configuration with an inverted T-shaped rail member 138 for engaging the tracks 136*a* and 136*b* of the milling block 100. The handle 140 has detent means 146 located in the center of the rail member 138 which fits into the depression 144 of the tracks 136*a* and 136*b* and functions to center and lock the handle 140 to the milling block 100.

Referring to FIG. 9, the distractor apparatus of the present invention generally referred to by the numeral 150 is shown in an exploded view in relation to milling block 100. The distractor apparatus 150. comprises a distractor 151 having a cylindrical shaft 152 with a bullet-shaped leading end 154. The distractor 151 is interposed in the disc space between two adjacent vertebrae and bears upon the endplates of the adjacent vertebrae to urge the vertebrae apart. The leading end 154 of the distractor 151 is a flattened member having a height that may correspond to the normal anatomic height of the disc space between two adjacent vertebrae in which the distractor 151 is to be inserted or may have a height that is less than the anatomic height of the disc space. It is appreciated that the distracted height of the disc space may be equal to, less or greater than the normal anatomic height of the disc space. The shaft 152 of the distractor 151 has a plurality of annular slots 156 for engaging the distractor holder 158.

The leading end 154 of the distractor 151 may have a height in the range of 4 mm to 20 mm, with 10 mm to 14 mm being the preferred height in the lumbar spine except for a collapsed and degenerated disc which may be less, 5.5 mm to 7.5 mm being the preferred height in the cervical spine. The distractor 151 may have a thickness in the range from 1 mm to as great as 20 mm in the cervical spine, with 2 mm being the preferred thickness. In the lumbar spine the distractor 151 may be from 2 mm to 50 mm thick with a range of 2 mm to 5 mm being preferred. The length of the portion of the leading end 154 distractor 151 extending beyond the front face 102 of the milling block 100 (referred to herein as the "penetration depth") is less than the depth of the disc space in that location. The "depth" of the disc space is the distance between the anterior and posterior aspect of a vertebrae; the "width" of the disc space is the distance between the lateral aspects of a vertebrae; and the "height" of the disc space is the distance between two vertebral endplates adjacent to the disc space. For the cervical spine, the length of distractor 151 would range from 8 mm to 20 mm, with 10–15 mm being preferred as measured at the sagittal (left from right) midline; while in the lumbar spine the distractor 151 length would range from 15 mm to 40 mm, with 20 mm to 35 mm being preferred.

Referring to FIGS. 9–10 the distractor holder 158 has an inverted Y-configuration with a central tubular member 160 and a base member 160. The bottom portion 164 of the tubular member 160 has side slots 166 having a width sufficient to accommodate the thickness of the leading end 154 of the distractor 151. Located over the bottom portion of the tubular member 160 is a sleeve 168 which engages the bottom portion 164 and rotates freely about the bottom portion 164 of the tubular member 160. The sleeve 168 has an external thread 170 for engaging the milling port 118 of the sliding mill guide 116 and knob 171 for rotating the sleeve 168. The sleeve 168 engages the opening 186 in the drill insertion end 184 of the calibration gauge 180 illustrated in FIG. 11A and described in detail below.

Depending from the base member 162 of the distractor holder 158 are posts 134*a* and 134*b* for centering and engaging the distractor holder 158 to the milling block 100 and to the distractor insertion end 182 of the calibration gauge 158. The posts 134*a* and 134*b* fit into the blind holes 130 and 132 of the milling block 100 and also fit into the blind holes 188*a* and 188*b* of the calibration gauge 180.

The upper portion 172 of the tubular member 160 of the distractor holder 158 has a spring loaded locking collar 174 for locking the distractor 151 to the distractor holder 158 after the distractor 151 is inserted into the distractor holder 158. The distractor holder 158 holds the distractor 151 with a spring loaded gripping member 176 that is configured to engage the annular slots 156 in the shaft 152 of the distractor 151. The locking collar 174 is locked and unlocked by the partial rotation of the locking collar 174 about the upper portion 170 of the tubular member 160. The locking collar 174 is kept in a "locked" or "unlocked" position by slot 173 and pin 175.

In the locked position, the locking collar 174 forces the gripping member 176 into the annular slots 156 of the shaft 152 of the distractor 151 to hold the distractor 151 within the distractor holder 158. The gripping member 176 has tynes 177 with an enlarged head portion 178 which has a complimentary configuration for fitting the annular slots 156 of the distractor 151. The gripping member 176 is locked by sliding the locking collar 174 in a direction away from the base 162 such that the locking collar 174 slides over the gripping member 176 to compress the tynes 177 into the slots 156. To unlock the distractor holder 158, the locking collar 174 is rotated and slid in the direction toward the base 162 to release the tynes 177 as shown in FIG. 9.

Referring to FIG. 11A, a calibration gauge 180 is shown for setting the depth of the distractor 151 within the distractor holder 158 and for setting the depth of the milling instrument 200 in the coupling member 208 described in detail below. The calibration gauge 180 has a substantially rectangular configuration with a distractor insertion end 182 and a drill insertion end 184. The distractor insertion end 182 has an opening 186 of a sufficient diameter for receiving the leading end 154 of the distractor 151 and a portion of the sleeve 168 of the distractor holder 158. The distractor insertion end 182, has two blind holes 188a and 188b for receiving the posts 134a and 134b of the distractor holder 158. Similarly, the drill insertion end 184 has an aperture 190 of a sufficient diameter for receiving and setting the depth of a milling instrument 200.

Figure 31:
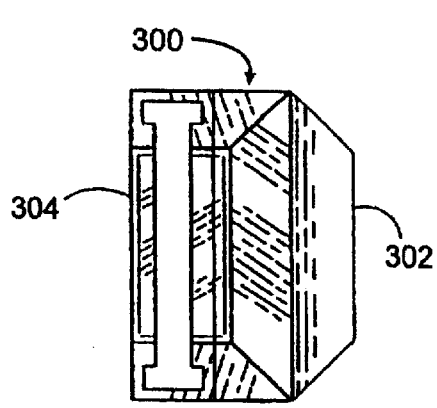
FIG. 31 is a side elevational view of the alternative embodiment of the milling block of the present invention shown in FIG. 27.
Figure 32:
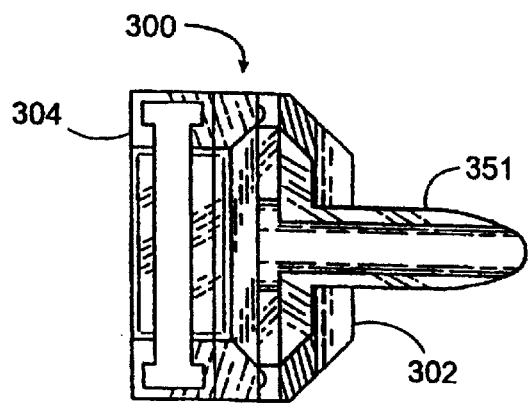
FIG. 32 is a side sectional view of the alternative embodiment of the milling block of the present invention shown in FIG. 27 with a distractor element inserted into the milling block.

Referring to FIGS. 11B and 11D, a side elevational view of a distractor 151 having parallel top and bottom sides 153a and 153b is shown inserted in the disc space between adjacent vertebrae $V_1$ and $V_2$. The distractor 151 is used to place and keep the two adjacent vertebrae $V_1$ and $V_2$ in parallel spatial relationship when the distractor 151 is inserted in the disc space with the top and bottom sides 153a and 153b placed against the vertebral endplates of the adjacent vertebrae $V_1$ and $V_2$. As shown in FIG. 31D, the distractor 151 is placed between two adjacent vertebral $V_1$ and $V_2$ to orient and maintain the vertebrae in parallel relationship to each other.

Referring to FIG. 11C and 11D, a side elevational view of distractor 151' is shown having top and bottom sides 153a' and 153b' in a converging annular relationship to each other. The distractor 151' is used to place and keep two adjacent vertebrae $V_2$ and $V_3$ in angular relationship to each other, such as where the restoration of lordosis is desired at a specific disc level of the spine. As shown in FIG. 11D, the distractor 151' is placed between two adjacent vertebrae $V_2$ and $V_3$ to orient and maintain the vertebrae in angular relationship to each other.

Referring to FIG. 12, the calibration gauge 180 for calibrating the depth of the distractor 151 within the distractor holder 158 is shown. The calibrator gauge 180 is hollow and has a window 192 with graduated marks 194 indicating the depth in which the distractor 151 being held by the distractor holder 158 will penetrate the disc space between two adjacent vertebrae when the distractor 151 is subsequently inserted into the disc space as described in detail below.

In one embodiment of the calibration gauge 180, for use in the cervical spine, the graduated marks 194 range from 11 to 21 mm to represent the length of insertion of the distractor 151 which penetrates the disc space. The distractor 151 is selected and inserted into the distractor holder 158 and remains in the unlocked position as shown in FIG. 12. The leading end 154 of the distractor 151 is then placed within the aperture 186 of the calibration gauge 180 such that the leading end 154 of the distractor 151 becomes visible through the window 192. The desired depth of the distractor 151 may be selected in reference to the graduated marks 194 by adjusting the distractor 151 in relation to the distractor holder 158 such that the desired amount of the distractor 151 extends within the calibration gauge 180. The depth adjustment of the distractor 151 is accomplished by sliding the shaft 151 the distractor 151 up or down in relation to the distractor holder 158. Once the correct depth suitable for the disc space in which the distractor 151 is to be inserted has been selected for the distractor 151, the locking collar. 174 on the distractor holder 158 is rotated and moved to compress the tynes 177 of the gripping member 176 into the annular slots 156 of the distractor 151 and the distractor 151 is held in fixed relationship to the distractor holder 158 at the desired depth. In the preferred embodiment, the annular slots 156 are spaced apart a distance corresponding to each of the graduated marks 194 to facilitate the depth selection and adjustment of the distractor 151 within the distractor holder 158. The distractor holder 158 is then dissociated from the calibration gauge 180 and the distractor 151 remains in fixed position in the distractor holder 158 since the distractor holder 158 is in the "locked" position. In the alternative, as shown in FIGS. 9 and 11A–11C, each of the annular rings 156 is numbered for length which can be read directly from the shaft 152 as the number appearing beyond the gripping member 176.

Figure 13:
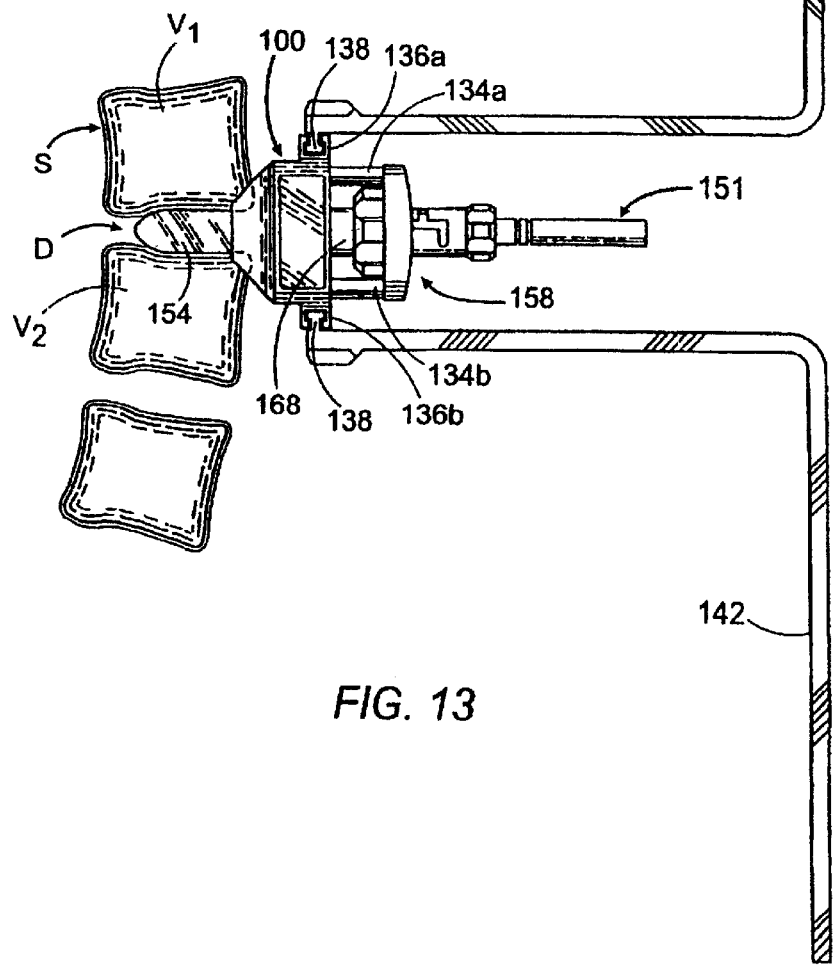
FIG. 13 is a side elevational view of the milling block of the present invention placed against the anterior aspect of a segment of the spine with the distractor holder coupled to the milling block and the distractor inserted in the disc space between two adjacent vertebrae and the handles attached to the milling block of the present invention.
Figure 14:
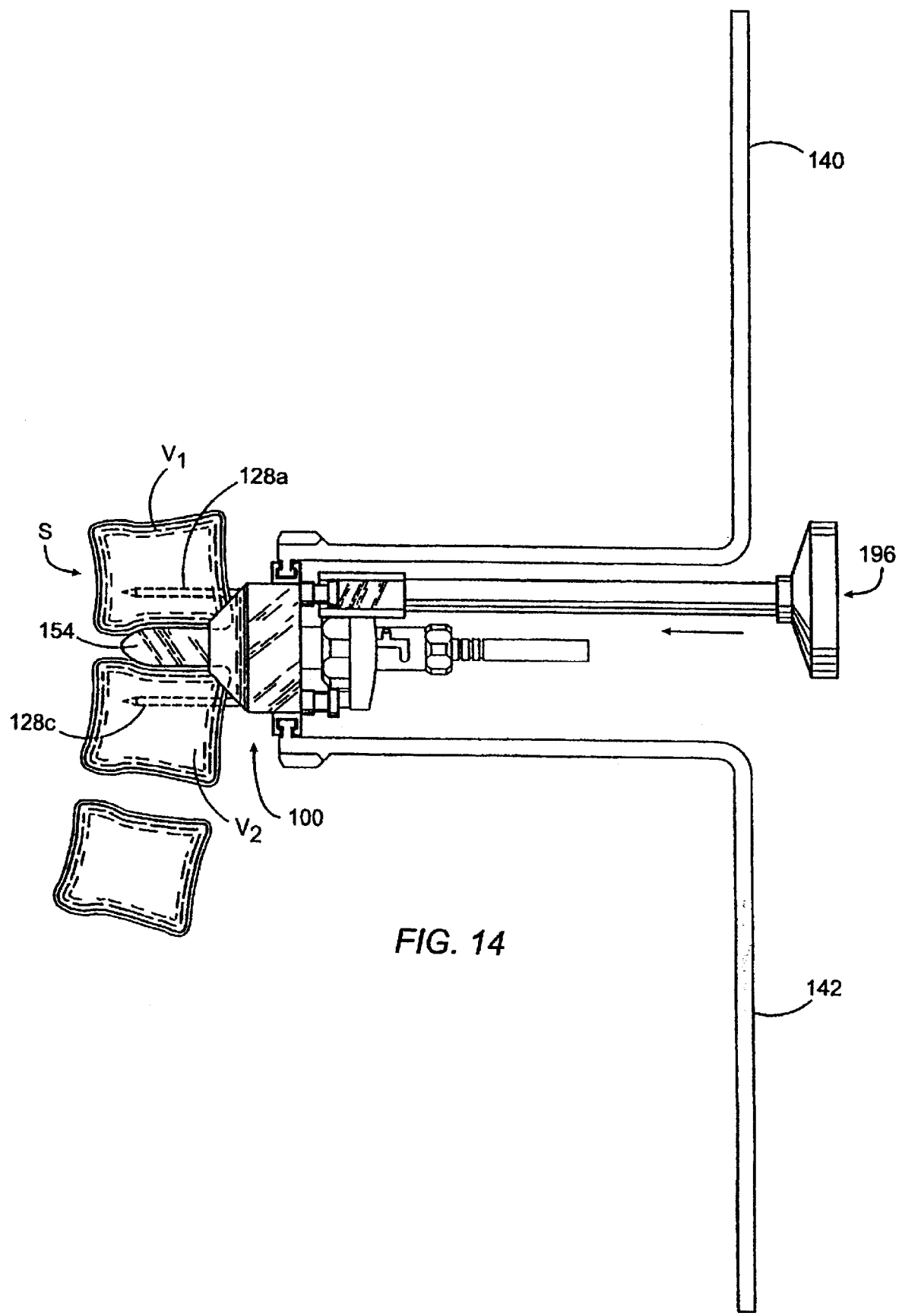
FIG. 14 is a side elevational view of the segment of the spine with the milling block of the present invention attached to the anterior aspect of the spine by a plurality of pins shown partially in hidden line and being driven by a pin driver.

Referring to FIGS. 13 and 14, the distractor holder 158 with the distractor 151 locked in place is coupled to the milling block 100 such that the leading end 154 of the distractor 151 passe's through the threaded port 118 of the mill guide 116. The posts 134a and, 134b of the distractor holder 158 are positioned within the blind holes 130 and 132 of the milling block 100 and the sleeve 168 of the distractor holder 158 is threadably coupled to the threaded collar port 118 of the milling block 100. The handles 140 and 142 are engaged to the milling block 100 with the rail member 138 in the tracks 136a and 136b and the detent means 146 positioned within the depression 144 of the tracks 136a and 136b.

The combined distractor apparatus 150 and milling block 100 assembly is then brought to the fusion site of the spine S from the anterior aspect of the spine S and the leading end 154 of the distractor 151 is then introduced into the disc space D between two adjacent vertebrae $V_1$ and $V_2$. It is appreciated that the distractor 151 may be introduced into the disc space D turned on its side (with the sides 153a and 153b parallel to the horizontal plane of the disc space D) so as to facilitate introduction of the distractor 151 into the disc space D and then turned 90 degrees position the sides 153a and 153b of the distractor 151 perpendicular to the horizontal plane of the disc space D to distract the vertebrae $V_1$ and $V_2$. Alternatively, the distractor 151 may be introduced with the sides 153a and 153b perpendicular to the horizontal plane of the disc space D, relying on the bullet-shaped leading edge 154 to distract the vertebrae $V_1$ and $V_2$ apart during insertion. The angular relationship of the two vertebrae $V_1$ and $V_2$ adjacent to the disc space D will then be determined by the shape of the distractor 151 as illustrated in FIG. 11D and previously described above.

Referring to FIGS. 14 and 15, the front face 102 of the milling block 100 is placed adjacent to the segment of the spine S in which the fusion or artificial disc implantation is being performed. The milling block 100 is then secured to the anterior aspect of the spine S by engaging each of the adjacent vertebrae $V_1$ and $V_2$ by inserting pins 128a–d with a pin driver 196. The pins 128a–d are inserted into the pin holes 120a–d and pass through the milling block 100 and penetrate the bone of the vertebrae $V_1$ and $V_2$ to engage the milling block 100 to the spine S. It is appreciated that while two pins 128 into each of the adjacent vertebrae are shown, other engaging means such as a screw, or more or less of such engaging means to engage the milling block 100 to the spine, could also be used, such as prongs fixedly attached and extending forward from the milling block 100. After the milling block 100 is secured to the vertebrae $V_1$ and $V_2$ of the spinal column, the distractor holder 158 and the distractor 151 are removed from the disc space D and the handles 140 and 142 are removed from the milling block 100 as shown in FIG. 15. It is now possible for the surgeon to view the vertebrae $V_1$ and $V_2$ through the central aperture 114 of the milling block 100 so that the width and depth of the desired bone resection from each of the adjacent vertebrae may then be easily confirmed visually prior to performing any actual bone resection.

Referring to FIGS. 16–18B, the milling apparatus of the present invention, generally referred to by the numeral 200 is shown. The milling apparatus 200 is a bone removal device used to mill (remove a portion of bone from) the endplates of the vertebrae $V_1$ and $V_2$ adjacent to the disc space D in which a spinal implant is to be inserted. The milling apparatus 200 comprises a milling bit 202 having a shaft 204 terminating in a cutting portion 206 having a cutting end and a cutting perimeter for cutting bone. The shaft 204 is configured to fit within a driver coupling member 208 for coupling the milling bit 202 to a driving device, well known in the art, such as motorized drill or gas driven turbine (not shown) The driver coupling member 208 has a shaft receiving end 210 for receiving the; shaft 204 of the milling bit 202, an annular segmented collar portion 212, and a driver coupling end 214 for coupling to a driving device. While gas driven turbines are known and are presently manufactured and sold by Midas Rex, Anspach, Zimmer, Inc. and others, all these units attach to a gas driven turbine and hold a burr, but lack any adjustable depth limiting means, such as the adjustable depth limiting means of the present invention so as to be able to be lockably engaged into a further apparatus such as is required in the present invention.

A locking adapter 216 functions to lock the milling bit 202 to the driver coupling member 208, to couple the milling bit 202 to the calibration gauge 180, and to couple the milling bit 202 to the port 118 of the mill guide 116 of the milling block 100. The locking adapter 216 comprises a hollow tubular sleeve 218 and has a similar configuration to the locking collar 174 of the distractor holder 158 described above. The sleeve 218 has a locking collar 220 and a spring-loaded gripping member 222 similar to the locking collar 174 and gripping member 176 described above. The locking adapter 216 has a bottom portion 224 of the sleeve 218 for coupling to the drill insertion end 184 of the calibration gauge 180. An adaptor fitting 226 is provided having a threaded portion 228 for engaging the threaded port 118 of the milling guide 116.

The proper diameter milling bit 202, corresponding to the space to be created Between the adjacent vertebrae is adjusted with the calibration gauge 180 to select the appropriate maximum safe penetration depth into the disc space of the milling bit 202 to prevent unwanted over penetration into the disc space. After the milling bit 202 is inserted into the calibration gauge 180, the length of the milling bit 202 that is capable of extending through the milling block 100 is adjusted in reference to the calibration marks 194 of the calibration gauge 180 and the milling bit 202 is then locked to the driver coupling member 208.

For example, it the desired length of the milling bit 202 extending into the milling block 100 is 15 mm (determined by the dimensions of the vertebrae being milled), then the milling apparatus 200 would be coupled to the calibration gauge 180 and the driver coupling member would be advanced toward the calibration gauge 180 until the tip of the cutting portion 206 is aligned with the graduated marks 194 corresponding to 15 mm. The locking adapter 216 is then rotated and placed in the locked position with the gripping member 222 engaging the segment on the collar portion 212 corresponding to 15 mm.

It is appreciated that other means for setting the depth of the milling bit 202 are contemplated to be within the scope of the present invention. For example, with reference to FIG. 18A the segments of the collar portion 212 of the milling apparatus 200 can include calibration marks corresponding to the depth of the milling bit 202 extending through and protruding from the milling block 100. In this manner, the gripping member 222 is set to engage the appropriate segment of the collar 212 corresponding to the desired depth Similarly, the annular slot 154 on the shaft 152 of the distractor 151 may include calibration marks for setting the desired depth of the distractor 151 without the use of a calibration gauge 180.

It is further appreciated that the milling apparatus may comprise any suitable bone removal means such as, but not limited to, burrs, router bits, abraders, grinders, rasps, drills, graters, saws, oscillating cutters, vibrating cutters, reciprocating cutters, orbital cutters, rotating cutters and lasers.

Figure 19:
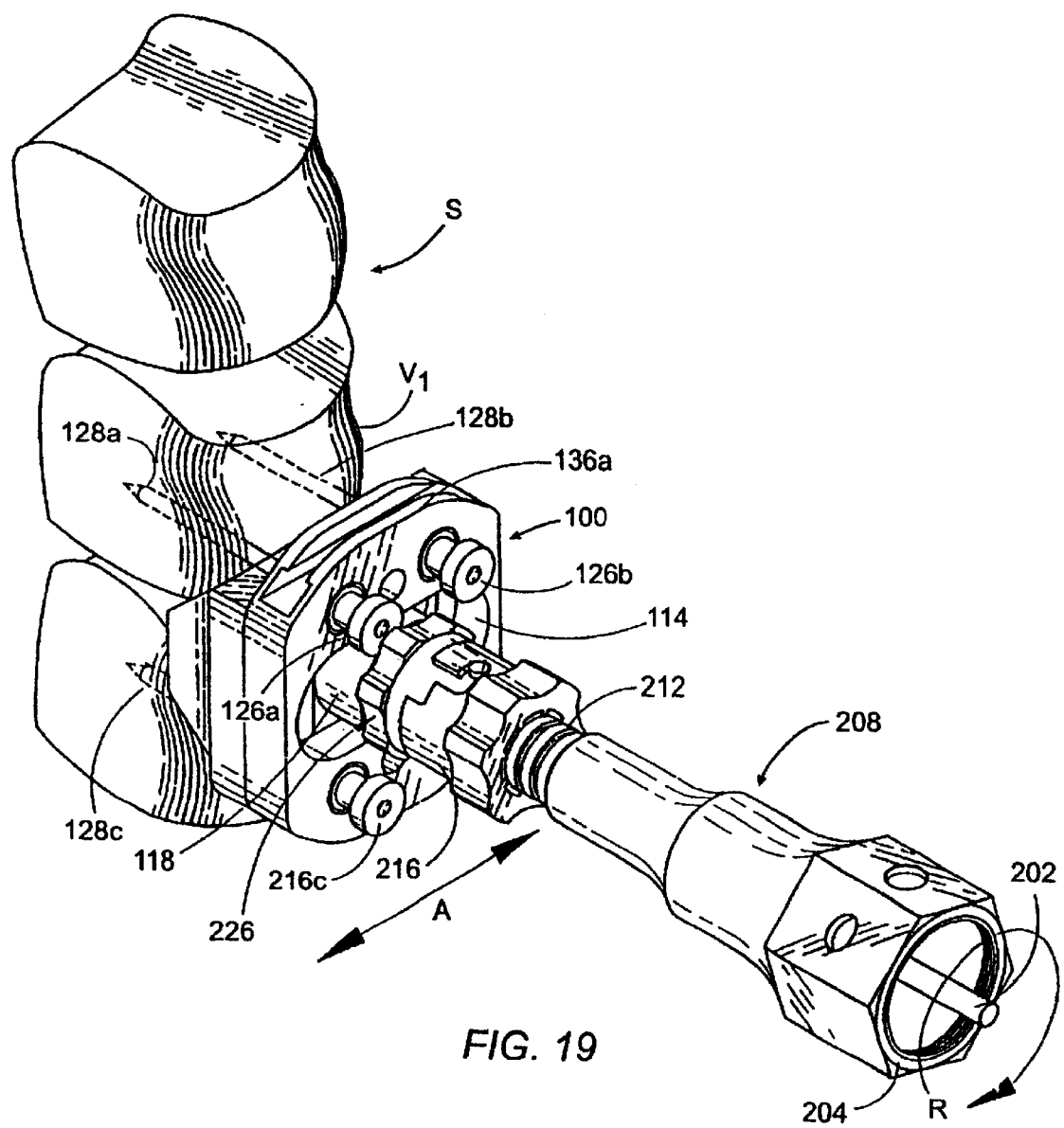
FIG. 19 is a side perspective view of the bone removal assembly coupled to a milling block of the present invention that is engaged to a segment of the spinal column by a plurality of pins shown partially in hidden line.

Referring to FIGS. 18B and 19, the milling apparatus 200 is then inserted through the adaptor fitting 226 and is screwed to the port 118 of the milling block 100. The milling bit 202 is then rotated at high speed as illustrated by arrow R in FIG. 19. The milling apparatus 200 rotating at high speed is moved in the direction illustrated by arrow A and the portions of the vertebrae $V_1$ and $V_2$ adjacent to the disc space are then milled to create a space for receiving an implant. After the creation of the space for the implant, the milling apparatus 200 is removed from the milling block 100 and the prepared space may be irrigated and suctioned through the port 118 of milling block 100, or alternatively the entire milling assembly including the milling block 100 may first be removed and the space then irrigated and suctioned. The disc space D is distracted utilizing conventional means and the appropriate implant or implants are then inserted into the newly prepared space.

Referring to FIGS. 20–22, a segment of the spinal column S is shown with an implant I inserted between the two adjacent vertebrae $V_1$ and $V_2$ in the space created with the milling instrumentation and method of the present invention. As shown in FIG. 22, the space B created by the milling block 100 is substantially rectangular in shape and extends across the width and length of the vertebrae $V_1$ and $V_2$ to create a large area of contact between the vertebrae $V_1$ and $V_2$ and the implant I, which may have a curved (from side to side) trailing end to conform to the curvature of the vertebrae.

Referring to FIG. 23, although implant I has been shown to have the substantially rectangular configuration it is appreciated that the implant I" can have a modified configuration with curved side walls (e.g. left and right) as shown in FIG. 23.

Referring to FIGS. 24–26, the space C created with the instrumentation and method of the prior art is shown with an implant I' inserted therein. In comparing the size of the space C with the size of the space B shown in FIG. 22 created by the method and instrumentation of the present invention, it is clear that the space B created with the instrumentation of the method of the present invention is substantially greater than was possible with the instrumentation and methods of the past. As a result, the spinal implant, I inserted in the space B can be substantially larger than implant I' and have a substantially greater surface area of contact with the vertebrae $V_1$ and $V_2$ providing greater stabilization to the segment of the spine S being fused.

Furthermore, it can be seen in FIG. 22 that with the present invention the implant can not only engage the very strong bone of the vertebral body at the endplate located posteriorly (in the back) and laterally (to each side), but as shown in FIG. 20, the implant may be embedded into sockets in the posterolateral corners of the vertebrae (dark shaded areas shown in FIGS. 20–26) providing enhanced stability to the implant which is blocked from moving more posteriorly or to either side.

Referring to FIGS. 27–35, an alternative embodiment of the milling block of the present invention is shown and generally referred to by the numeral 300. The milling block 300 has a similar configuration to the milling block 100 described above, and comprises a modified distractor element 351 for separating and orienting the adjacent vertebrae in the appropriate relationship to each other prior to milling the space in which an implant is to be inserted. The distractor element 351 is inserted in an inverted T-shaped slot 301 in the front face 302 of the milling block 300. The slot 301 comprises a spring loaded detent means 303 which functions to hold the distractor member 351 in place once it is inserted within the slot 301.

Figure 30:
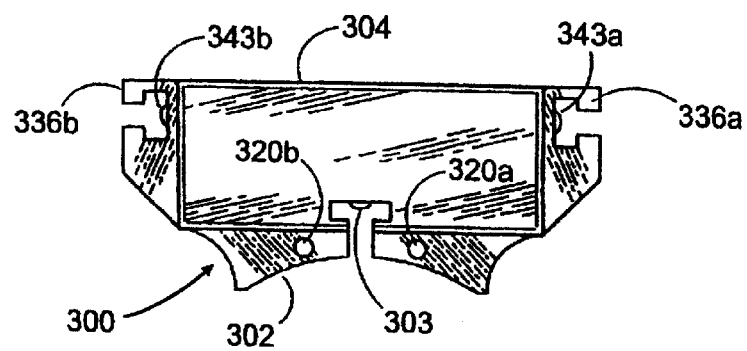
FIG. 30 is a top plan view of an alternative embodiment of the alternative embodiment of the milling block of the present invention shown in FIG. 27.
Figure 27:
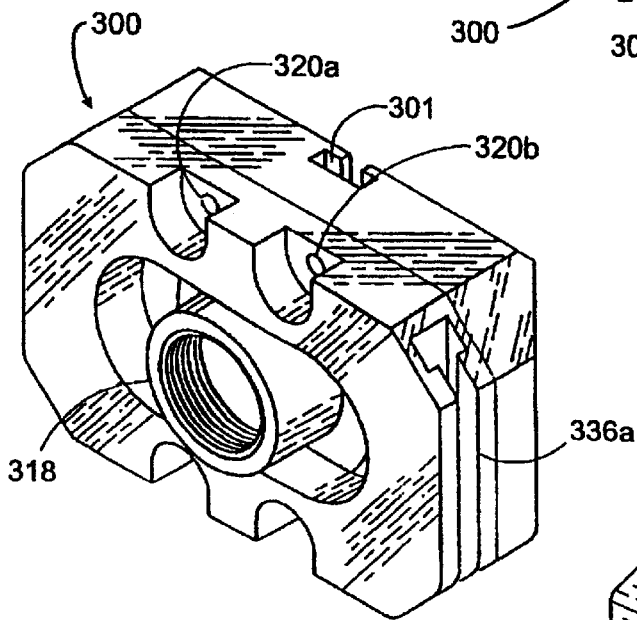
FIG. 27 is a rear perspective view of an alternative embodiment of the milling block of the present invention.
Figure 29:
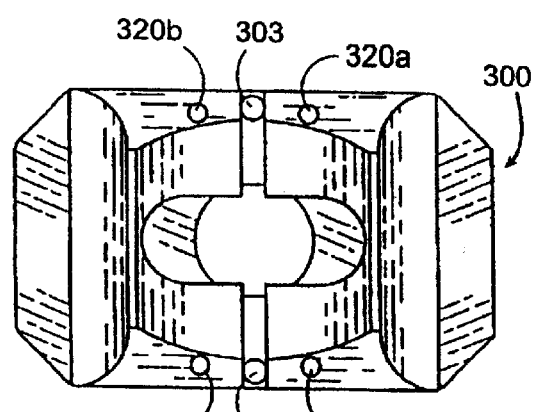
FIG. 29 is a front elevational view of the alternative embodiment of the milling block of the present invention shown in FIG. 27.
Figure 28:
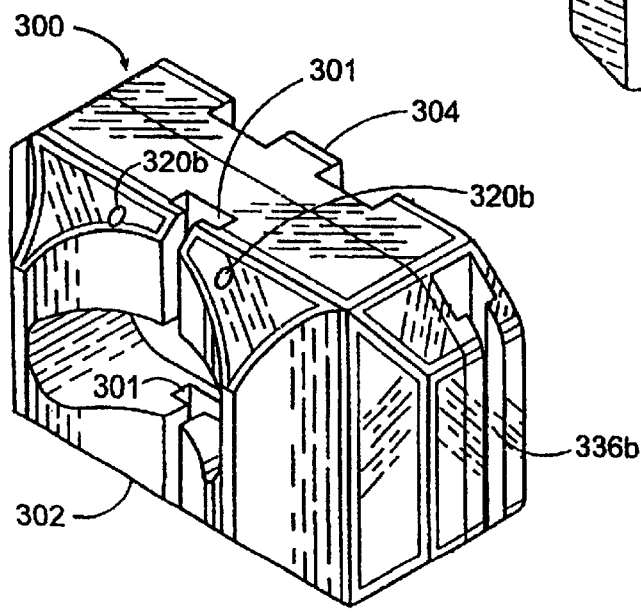
FIG. 28 is a front perspective view of the alternative embodiment of the milling block of the present invention shown in FIG. 27.
Figure 33:
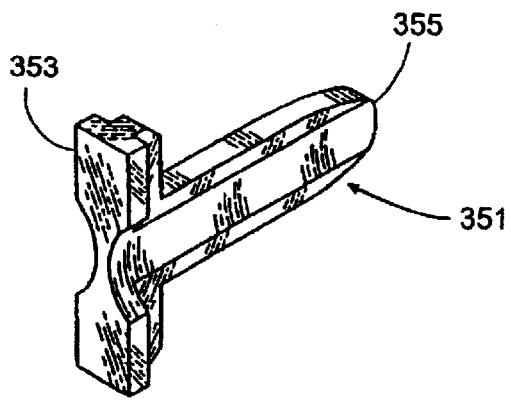
FIG. 33 is a side perspective view of the alternative embodiment of the distractor element of the milling block of the present invention.
Figure 34:
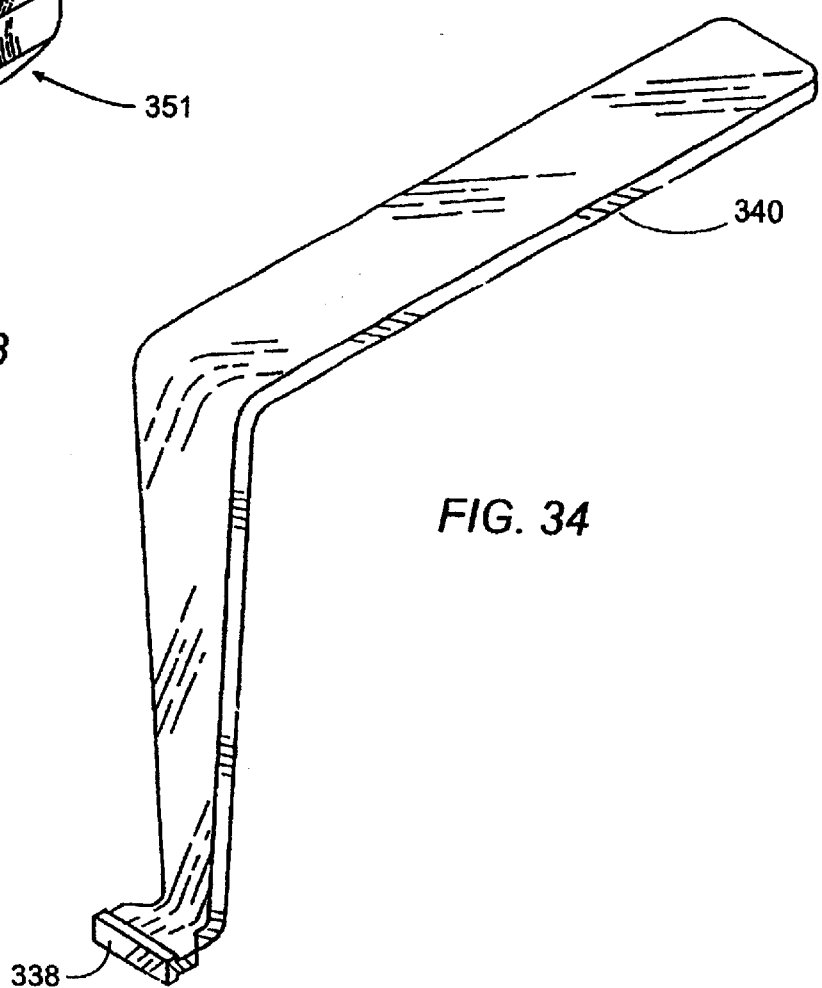
FIG. 34 is a side perspective view of an alternative embodiment of the handle used to hold the milling block of the present invention.
Figure 35:
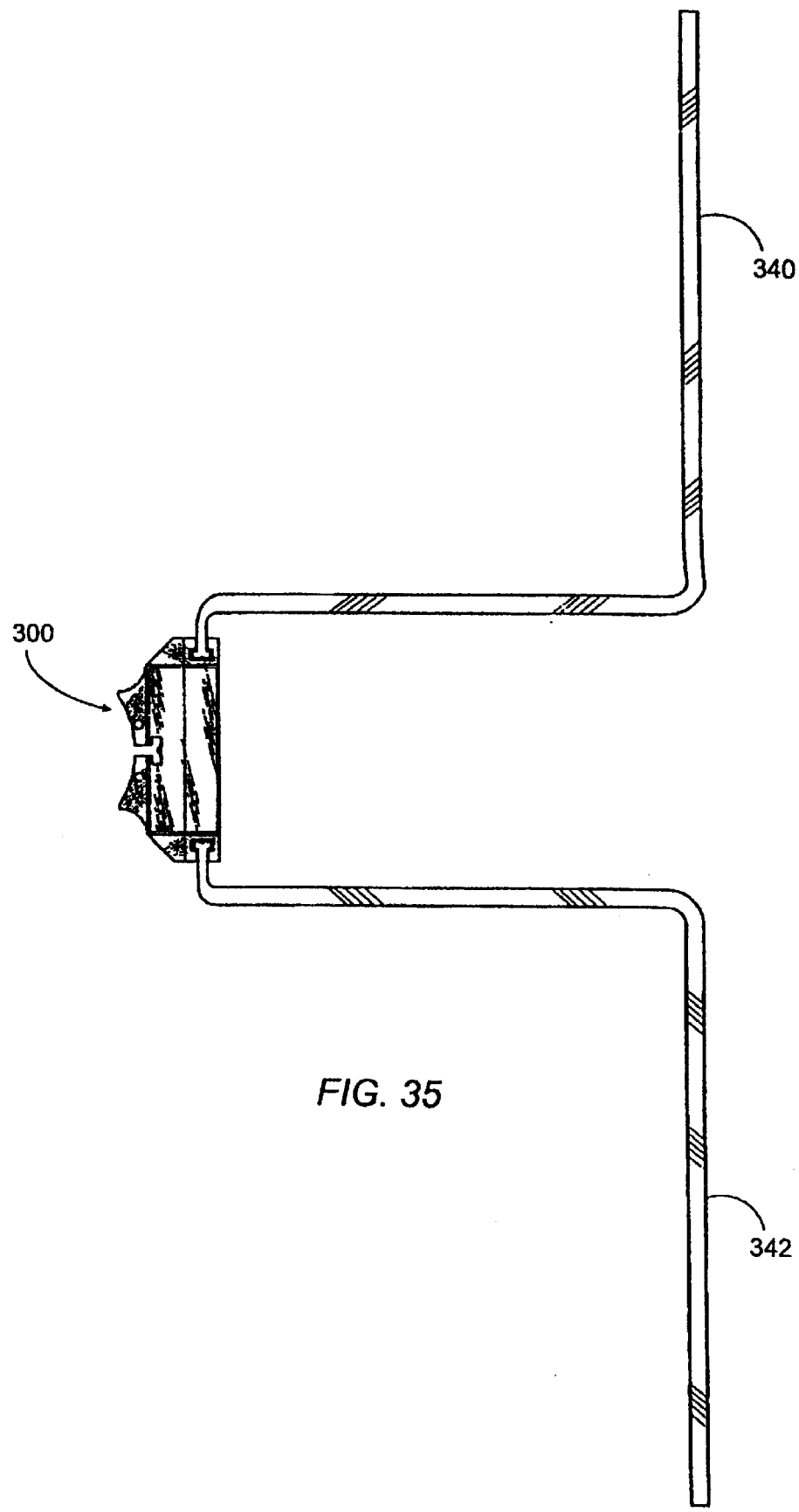
FIG. 35 is a side elevational view of the alternative embodiment of the milling block of FIG. 27 with a pair of detachable handles shown attached to the milling block.

Referring to FIG. 33 a perspective view of the distractor element 351 is shown having an inverted T-shaped rail member 353 which corresponds in configuration to the inverted T-shaped slot 301. The distractor element 351 has an insertion end 355 that is tapered and bullet shaped to facilitate insertion into the disc space D between two adjacent vertebrae $V_1$ and $V_2$. The distractor element 351 is inserted into the slot 301 of the milling block 300 prior to attaching the milling block 300 to the segment of the spine S in which the fusion is desired. The distractor element 351 has a biconcave configuration to conform to the curvature of the cutting end 206 of the milling bit 202 of the milling apparatus 200, as described above, such that the horizontal excursion of milling bit 202 on either side of the distractor element 351 is maximized when used to create a space in the adjacent vertebrae $V_1$ and $V_2$. It is appreciated that the distractor element 351 may come in different lengths in order to accommodate for the different dimensions of the disc space between the two adjacent vertebrae in which the surgical procedure is to be performed. referring to FIGS. 30 and 35, the track members 336a and 336b are located-on the sides of the milling block 300 such that handles 340 and 342 may be attached to the milling block 300 as previously described herein. The track members 336a and 336b each have a detent means 343a and 343b, respectively, for holding the handles 340 and 342 as shown in FIG. 30.

Referring to FIG. 36–37, an alternative embodiment of the milling apparatus generally referred to by the number 361 is shown. The milling apparatus 361 comprises a coupling member 308 which is identical to coupling member 208 previously described. The milling apparatus 361 includes a milling bit 365 with a cutting portion 367 and a shaft portion 369 that are similar to the milling bit 202 previously described. Milling bits such as 365 are known and commercially available. The element of milling bit 365 as well as the use of an element such as milling bit 365 with a coupling means such as coupling member 308 are well known in the art. An adaptor sleeve 371 is used to couple the coupling member 308 and the milling bit 365 to the port 318 of the milling block 300. The sleeve 371 comes in a variety of lengths depending on the desired depth of the space to be created and functions to limit the excursion of the milling bit 365 into the milling block 300. The longer the sleeve 371, the less the excursion of the milling bit 365 into the disc space between two adjacent vertebrae in which the opening is desire to be created. Thus, the surgeon can predetermine the depth of the space being created by selecting the appropriate sleeve 371 length prior to performing the procedure.

Referring to FIGS. 38–42 an alternative embodiment of the milling block of the present invention is shown and generally referred to by the numeral 400. The milling block 400 comprises a central template 401 for creating a space of any desired shape and as an example, the space to be created may be a substantially rectangular space corresponding to the shape of the rectangular template 401. The template 401 has a track 407 passing through the milling block 400 from the rear face 404 to the front face 402 of the milling block 400. The track 407 is configured to receive a suitable bone removal means such as a drill a router or a laser, and the like, to remove a portion of the bone of the adjacent vertebrae milling instrument 403 and serves as a guide for creating the desired space in the adjacent vertebrae with a suitable bone removal means including, but not limited to, a router, to remove a portion of the bone of the adjacent vertebrae. The milling instrument 403 is inserted into a collar 405 which fits into the track 407 and is retained in slidable relationship within the track 407 of the template 401 and functions to guide the travel of the milling instrument 403 within the track 407. The drilling instrument 403 is then activated and moved within the confines of the track 407 to create the desired space in the vertebrae, which space can be of a shape corresponding to the shape of track 407 of the template 401. This is particularly useful for creating a shape, such as that shown in FIG. 45, which might be desirable for installing an artificial disc device 409 between two adjacent vertebrae.

Referring to FIGS. 43 and 44, alternative embodiments of the milling block 400 designated as 400' and 400" are shown engaging two adjacent vertebrae $V_1$ and $V_2$ shown in hidden line.

Tracks 401' and 407" are configured to Create a space such as shown in FIG. 44 for receiving an artificial implant or an artificial joint as shown in FIG. 45. It is appreciated that in addition to the foregoing configurations of the template 400, that other configurations are possible and contemplated to be part of the present invention.

Referring to FIGS. 46 and 47 an alternative embodiment of the milling block of the present invention is shown and generally referred to by the numeral 500. The milling block 500 is similar in configuration to the milling block 300 previously described above and comprises a pair of removable distractor elements 551a and 551b which are inserted in complimentary inverted T-shaped slots 553a and 553b at opposite sides of the milling block 500. The distractor elements 551a and 551b are inserted in the disc space D and function to restore the height of the disc space D prior to the milling operation to create the desired space. The distractor elements 551a and 551b are oriented at the sides of the central aperture 514 and each have a concave surface facing the central aperture 514 to conform to the curvature of the milling instrument such as milling bit 206, used to create the space between the two adjacent vertebrae. The lateral placement of the distractor elements 551a and 551b allows for the full side-to-side motion of the milling guide 516 to permit the unimpeded milling and creation of the space and without the need for having to remove and reinsert the milling instrument in order to get around a centrally placed distractor element such as distractor element 351 shown in FIG. 32.

Referring to FIGS. 48–49, an alternative embodiment of the milling block assembly of the present invention is shown and generally referred to by the numeral 600. The milling block 600 is substantially the same as the milling block 500 described above except that the pair of distractor elements 651a and 651b are joined at their distal ends by a cross bar 655. Cross bar 655 serves as a depth limiting means to any debris and to keep the pair of distractor elements 651a and 651b together as a unit.

Referring specifically to FIG. 50, an alternative embodiment of the milling block 600' is shown and generally referred to by the numeral 600'. The milling block 600' instead of utilizing pins 128a–128d to engage the vertebrae, a centrally placed prongs 603a and 603b to engage the milling block 600' to the adjacent vertebrae. The prongs 603a and 603b are an integral part of the milling block 600' or may also be removable, like pins 128a–d discussed above, as an example. It is further appreciated that the milling block 600 may engage the adjacent vertebrae via the distractor elements 651a and 651b positioned within the disc space to secure the milling block 600 to the spine. The tension forces generated by the distraction of the disc space from the insertion of the distractor elements 651a and 651b engage the vertebrae to the distractor elements 651a and 651b and functions to hold the milling block 600 to the spine.

Referring to FIGS. 51–57, the preferred embodiment of the milling block for use in the cervical spine of the present invention generally referred to by the number 700 is shown. The milling block 700 is shown with a distractor holder 758 which is capable of being coupled directly to the milling block 700. The distractor holder 758 has a pair of rotating post members 734a 734b and foot portions 737a and 737b, respectively, and handle portions 774a and 774b, respectively. The rear surface 704 of the milling block 700 comprises pin grooves 721a–721d for receiving pins, such as pins 128, previously described. The rear surface 704 also includes post grooves 723a and 723b for receiving the post members 734a and 734b in which the foot portions 737a and 737b of the post members 734a and 734b engage the lips of the post grooves 723a and 723b to lock the distractor holder 758 to the milling block 700.

The distractor holder 758 comprises of a gripping portion 776, similar to gripping member 176 previously described, for engaging a distractor, such as distractor 150 previously described. The distractor holder 758 is capable of locking the distractor 150 in the desired position in order to limit the excursion of the distractor end 154 into the disc space.

Referring specifically to FIG. 57, a fragmentary perspective view of the post member 734a is shown having a spring loaded detent means 790. The detent means 790 is seated in a recess 791 and is biased by spring 792, functions to lock the rotating post member 734a in place once engaged to the milling block 700. Prior to engaging the distractor holder 758 to the milling block 700, the desired length of the distractor 150 is set by engaging the calibration gauge 780 having one end capable of receiving the distractor holder 758. The depth of the distractor 750 is set according to the graduated marks 794 on the calibration gauge 780, or in the alternative as previously described by reference to the depth markings on the annular rings of the distractor. Once the desired length is selected, the distractor holder 758 is locked onto the distractor 750 in the same manner described above. The distractor holder 758 is then coupled to the milling block 700 with the sleeve 764 engaging the port 718 of the milling block 700. The post members 734a and 734b are then locked into place by rotating the handle portions 774a and 774b so that the foot portions 737a and 737b are engaging the post grooves 723a and 723b of the rear surface 704 of the milling block 700. Once the distractor holder 758 is engaged to the milling block 700, the pins, such as pins 128a–d, are inserted into the pin holes 721a–721d and the milling block 700 is engaged to the adjacent vertebrae.

After the milling block 700 is engaged to the adjacent vertebrae, the distractor holder 758 is removed and the adjacent vertebrae are held in the correct spatial relationship by the milling block 700 and pins 128a–d. It is appreciated that to facilitate the engagement and removal of the distractor holder 758, the calibration gauge 780 has a receiving end 781 for engaging the shaft to the distractor 151 such that the distractor holder 758 and distractor can be manipulated with the calibration gauge 780 serving as a handle. In this embodiment the distractor 151 has a flattened end portion 152 with a detent 155 as shown in FIG. 11A, to couple the distractor 151 to the calibration gauge 780.

The preparation and creation of the space between the adjacent vertebrae with milling block 700 is performed in the similar manner described above with a milling apparatus such as milling apparat 200 described above and shown in FIG. 16.

Referring to FIGS. 59–61, an alternative embodiment of the milling block of the present invention is shown and generally referred to by the numeral 800. The milling block 800 comprises of a template 801 having a narrow track 807 for receiving a bone removal device such as an oscillating blade 809 as shown in FIG. 61. The narrow track 807 functions to support and guide the motion of the oscillating blade 809 in the selected path of the track 807. Therefore, the track 807 can function as both means for accessing the adjacent vertebrae $V_1$ and $V_2$ and as a guiding means for guiding a bone removal instrument. The oscillating blade 809 is used to cut the desired space in the adjacent vertebrae along the track 807 of the template 801. As shown in FIG. 59 the template 800 Is engaged to two adjacent vertebrae shown in hidden line. The milling block 801 maintains the vertebrae $V_1$ and $V_2$ in the correct spatial relationship and the cutting of the bone is performed with the oscillating blade 809 to create the desired space. While slotted cutting fixtures are known in the field of orthopedic surgery, their purose is to resect the end of a long bone, and not a spinal vertebrae; and all examples known to this author work on but a single bone, do not attach to both of the bones that would from a joint and do not fix those bones in a desired spatial and angular relationship so as to create the optimal joint space and conformation.

Referring to FIG. 61 the saw housing 812 lockably engages the saw blade 809 by screw 811 within slot 810, which coupling means allows the protruding portion of blade 809 to be adjusted for length.

Referring to FIGS. 62 and 63, an alternative embodiment of the milling block apparatus of the present invention is shown and generally referred to by the numeral 900. The milling block apparatus 900 is suitable for use in procedures in which the surgeon's hand is at a point remote from the site of the spinal fusion, such as for use in endoscopic procedures, or for performing procedures on the posterior aspect of the spine on either side of the mid-sagittal axis of the vertebrae avoiding the spinal cord and other delicate structures present at the posterior aspect of the spine. The milling block apparatus 900 comprises an elongated member such as a hollow tube 901 having a front end 902 and a rear end 904 with milling guides 916a and 916b at each of its ends 902 and 904 for guiding a milling apparatus for creating and preparing the space between the two adjacent vertebrae. Such a milling apparatus would be similar to the milling bit 202 described above, and would have a shaft of sufficient length to span the distance between the milling guides 916a and 916b and have a cutting portion capable of passing through the ports 918a and 918b and extending into the disc space from the front end 902 of the milling block apparatus 900 for milling the bone of the adjacent vertebrae. In this manner, the desired space for receiving an implant may be created from a position remote from the spine such as would be useful for endoscopic spinal surgery.

The milling block apparatus 900 may be placed directly against the site of the spine in which the procedure is to be performed, with the front end 902 placed across the disc space and contacting the vertebrae adjacent to that disc space. The milling procedure for removing a portion of bone from the adjacent vertebrae to create a space for receiving an implant is performed with a bone removal means as discussed above for the other embodiments of the present invention.

Figure 64:
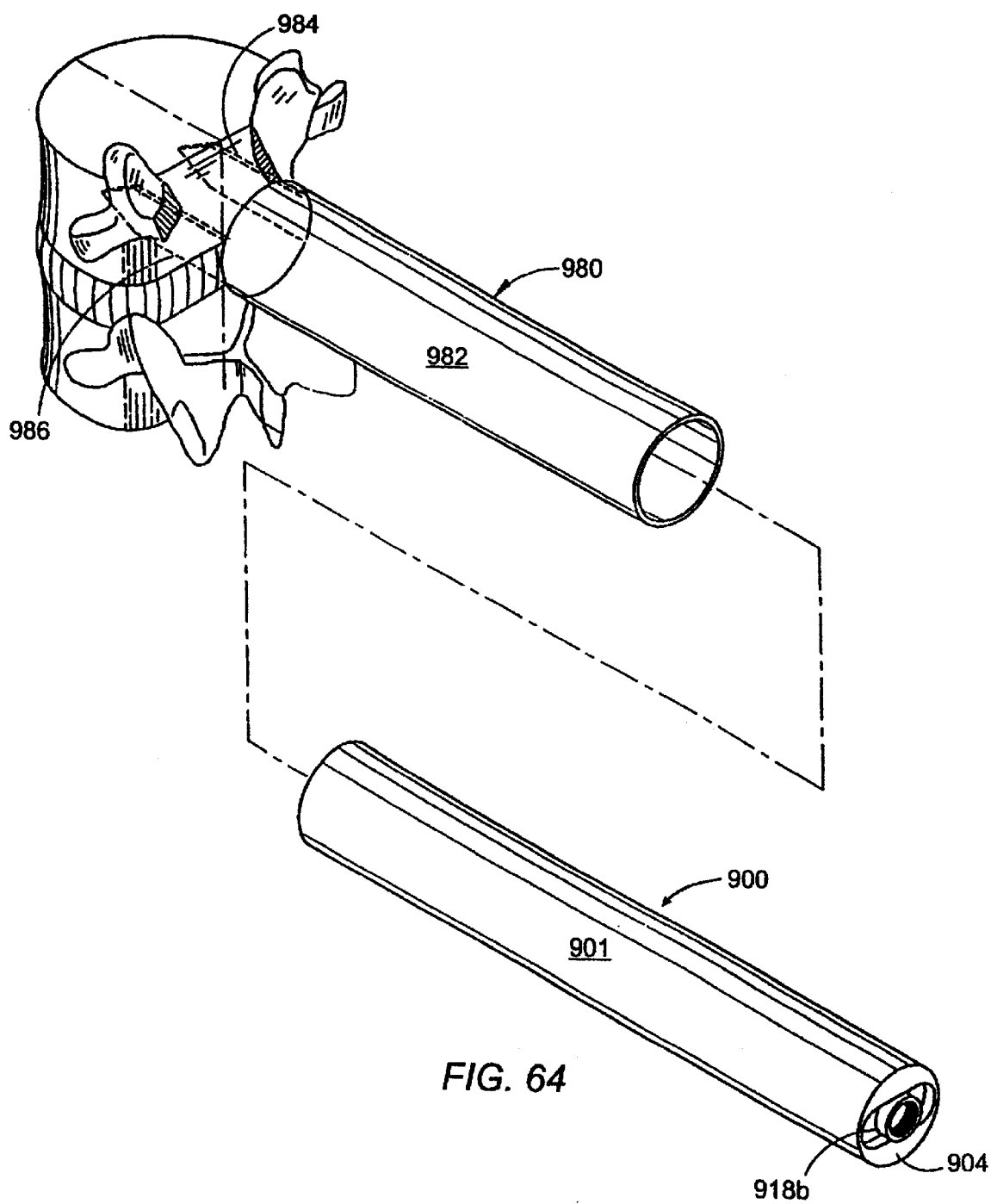
FIG. 64 is an exploded perspective view of a combined outer sleeve and distractor engaging two adjacent vertebrae and the milling block of FIG. 62 about to be inserted into the outer sleeve.

Referring to FIG. 64, the milling block apparatus 900 may be placed through a combination outer sleeve distractor 980 having a hollow sleeve portion 982 and having extensions members 984 and 986 extending from one end of the sleeve portion 982 for insertion into the disc space. The extension member 984 and 986 function to distract the disc space to its normal height and to engage the combination outer sleeve distractor 980 to the spine. The combination outer sleeve distractor 980 is capable of receiving and guiding the milling block apparatus 900 to the appropriate site in which the milling procedure is to be performed. The elongated tubular body 901 of milling block apparatus 900 would in use pass through the combined outer sleeve distractor 980, which itself would engage the spine at or adjacent to the disc space to be milled and would itself extend from the spine to outside of the patient's body. Such a combined outer sleeve distractor is taught by Michelson in co-pending application Ser. No. 08/396,414 filed on Feb. 27, 1995, incorporated herein by reference.

The bone removal from the adjacent vertebrae for creating the space for receiving an implant is performed with the milling block apparatus 900 positioned within the combination outer sleeve distractor 980 with a bone removal device passing through the ports 918a and 918b of the sliding mill guides 916a and 916b.

Figure 65:
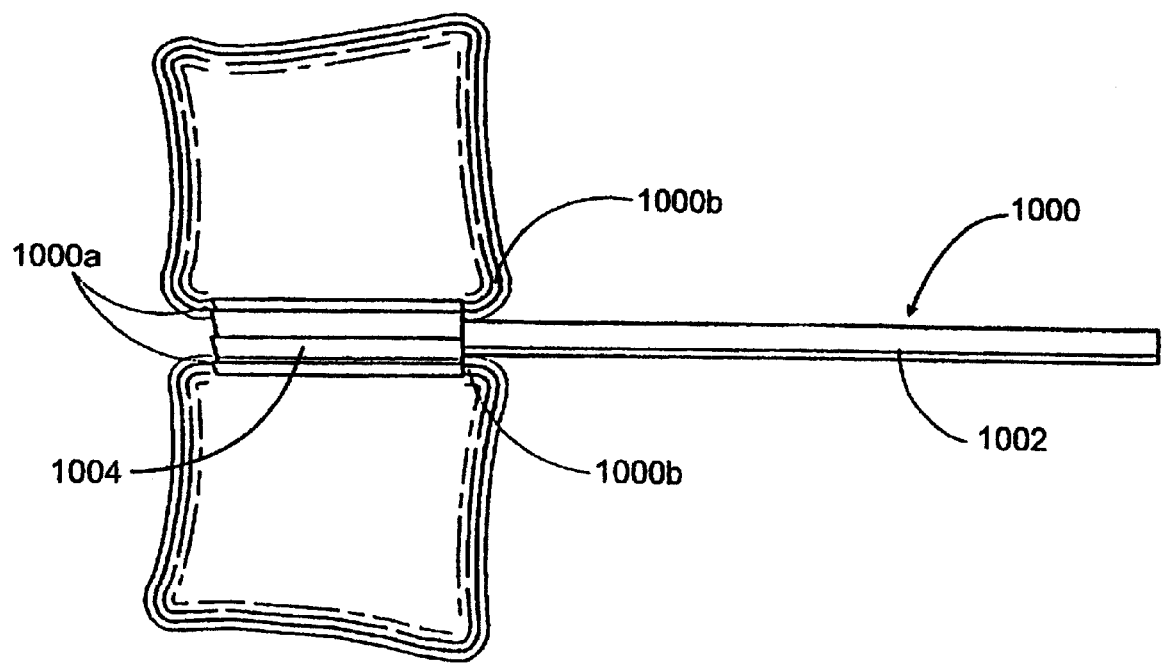
FIG. 65 is a side elevational view of the segment of the human spine with a milling instrument interposed between two adjacent vertebrae for preparing a disc space having anterior and posterior retaining walls for retaining an implant.

The milling block 900 as here taught need not be cylindrical and can be any shape, for example, square or rectangular to conform to the shape of the combination outer sleeve distractor 980. Furthermore, any such extended milling block 900 may have a flange proximally (rear end) or threads, or other means to fix, its position relative to said outer sleeve Referring to FIG. 65, a side view of a segment of the human spine with two adjacent vertebrae having a milling apparatus 1000 having a shaft 1002 and a cutting portion 1004 for preparing a space for receiving an implant, in which both the anterior and posterior aspects of the adjacent vertebral endplates have bone retaining walls 1000a and 1000b, respectively. The anterior and posterior retaining walls are created by the cutting portion 1004 having a larger diameter than the shaft 1002 of the milling apparatus 1000 and a length which fits within the depth of the adjacent vertebrae. Such a configuration permits the placement of substantially rectangular implant within the prepared space. The retaining walls 1000a and 1000b in the anterior and posterior aspects of the endplates function to lock and secure an implant or bone graft once installed between the two adjacent vertebrae.

While one particular type of bone milling instrument capable of cutting both on its leading end and along its sides has been shown a variety of bone cutting or abrading instruments including a drill rasp, burr, abraider or even a saw blade edge of the oscillating type or other could be used. Further, while the preferred embodiment bone milling means is shown as having a length extending at least as long as the depth of bone to be removed, the bone removal means can have a variety of shapes and lengths.

Referring to FIGS. 66 and 67, an alternative embodiment of the milling block, generally referred to by the numeral 1100 is shown. The milling block 1100 comprises two separable members: an instrument guiding member 1110 and a distractor base,member 1112. The distractor base member 1112 has a generally rectangular upper portion 1113 having a front face 1102 and a rear face 1104. The front face 1102 has a concave configuration that conforms to the natural curvature of a segment of the human spinal column and permits the placement of the front face 1102 of the milling block 1100 in close proximity to the spinal column. The upper portion 1113 of the distractor base member 1112 has a recess 1115 for receiving and holding a portion 1119 of the instrument guiding member 1110 of the milling block 1100 and a central opening 1117 through the center of upper portion 1113. The opening 1117 is preferably oblong-shaped, having an approximate width of 18–30 mm for use in the cervical spine, 30–50 mm for use in the lumbar spine, and if the milling block 1100 is used on the left and right sides of the mid-sagittal axis of a lumbar vertebrae separately, the approximate width of the opening 1114 is 15–25 mm and the approximate height of the opening 1114 is 5–20 mm.

Extending from the upper portion 1113 and extending beyond the front face 1102 are a pair of distractor elements 1151a and 1151b similar in configuration to the distractor elements 651a and 651b previously described above. The distractor elements 1151a and 1151b are capable of being introduced into the disc space between two adjacent vertebrae to place the vertebrae in a selected spatial relationship. The insertion of the distractor elements 1151a and 1151b into the disc space also functions to engage the distractor base member 1112 to the adjacent vertebrae.

The instrument guiding member 1110 of the milling block 1100 has a leading surface 1162, a trailing surface 1160, and a central aperture 1114 through its center having a suitable configuration corresponding to the central opening 1117 of the distractor base member 1112. Located within the aperture 1114 is a sliding mill guide 1116 having a threaded port 1118 for engaging various instrumentation as previously discussed in detail above. The mill guide 1116 slides in a transverse motion from side to side within the central aperture 1114 along the transverse axis of the aperture 1114.

The leading surface 1162 of the instrument guiding member 1110 is capable of interfacing with the rear face 1104 of the distractor base member 1112 and at least portion 1119 of the instrument guiding member 1110 is capable of being seated within the recess 1115 of the distractor base member 1112. After the distractor base member 1112 is engaged to the spine with the distractor elements 1151a and 1152b inserted into the disc space between two adjacent vertebrae and the instrument guiding member 1110 is seated into the distractor base member 1112, the removal of bone from the adjacent vertebrae is performed in the same manner as the milling procedure described above.

The milling block 1100 provides the added advantages of allowing the removal of the instrument guiding member 1110 while the distractor base member 1112 remains engaged to the spine maintaining the disc space distracted with the adjacent vertebrae in the appropriate spatial relationship to each other. With the distractor base member 1112 still engaged to the spine, it is possible to introduce an implant through the central opening 1117 and into the space for receiving the implant that has been created across the disc space and into the adjacent vertebrae. After the implant has been inserted into the disc space, the distractor base member 1112 is removed and the implant remains in the space created with the milling apparatus of the present invention.

Referring to FIGS. 68–72, an alternative embodiment of the milling block of the present Invention is shown and generally referred to by the numeral 1200. The milling block 1200 has a body member 1201 that is capable of extending across the disc space D and capable of engaging at least one of the vertebrae adjacent to the disc space D. The body member 1201 has a front face 1202, an opposite rear face 1204 and a curved central portion 1205. It is appreciated that the central portion 1205 need not be curved. The front face 1202 has a surface that permits the placement of the milling block 1200 against the vertebrae. The milling block 1200 has a central aperture 1214 through the center of the body member 1201 for accessing the disc space D between two adjacent vertebrae. Located within the aperture 1214 is a sliding mill guide 1216 having a groove 1217 for slideably engaging the body member 1201 to permit slideable movement of the mill guide 1216 relative to the body member 1201. The mill guide 1216 has a central opening 1219 in communication with the central aperture 1214 and a sliding member 1221 within the central opening 1219 having a port 1218 for coupling the sliding member 1221 to an instrument such as a destractor previously described, or a bone removal device, such as milling apparatus 200 previously described. It is appreciated that the mill guide 1216 in addition to guiding a milling apparatus 200, is also capable of guiding other instruments into the disc space such as a distractor element used to align the vertebrae and to distract the disc space.

The sliding member 1221 of the mill guide 1216 is capable of transverse motion from one side to the other side of the central opening 1219 along the transverse axis of the opening 1219 to guide and control a bone removal device, such as milling apparatus 200, in a selected transverse path relative to the vertebrae adjacent to the disc space D to remove at least a portion of bone from the vertebrae. The mill guide 1216 of the milling block 1200 is also capable of moving up and down in a vertical direction within the central aperture 1214 along the vertical axis of the aperture 1214, and along the curved central portion 1205 of the body member 1201. The vertical motion of the mill guide 1216 guides and controls the milling apparatus 200 in a selected path that may be at an angle to the vertebrae in order to remove an angular portion of bone from the vertebrae. The angular orientation of the milling apparatus 1216 relative to the vertebrae is a result of the position of the mill guide 1216 along the curved central portion 1205 of the body member 1201. In this manner, an opening having an angular configuration may be created, and with an appropriate implant placed within the prepared opening, the normal anatomic lordotic relationship of the vertebrae adjacent to the disc space D may be restored. Or in the alternative, the vertebrae adjacent to the disc space D could be placed in angular relationship prior to the removal of at least a portion of bone from the vertebrae, or a frusto-conical shaped bone removal device could be employed.

The milling block 1200 has a plurality of screw holes 1220*a–b* which pass through the milling block 1200 from the rear face 1204 through the front face 1202. The screw holes 1220*a–b* receive screws 1228*a–b* for engaging the milling block 1200 to the vertebrae adjacent to the disc space D. Similarly, pins, pegs or other suitable means for attaching the milling block 1200 to the vertebrae adjacent to the disc space D could be utilized.

While the present invention has been described in detail with regards to the preferred embodiment, it is appreciated that other variations of the present invention may be devised which do not depart from the inventive concept of the present invention.

What is claimed is:

1. An apparatus adapted for use in spinal surgery for creating an implantation space of selected shapes and dimensions at least in part within and across the height of the disc space between two adjacent vertebral bodies of the spine, each of the adjacent vertebral bodies having an endplate adjacent to the disc space, said apparatus comprising:

a milling block configured at least in part for placement across the height of the disc space and against at least a portion of the outer surfaces of the two adjacent vertebral bodies, said milling block having a leading face for placement against the two adjacent vertebral bodies and an opposite trailing face, said milling block having a width and at least one non-circular access aperture configured to provide access for the width of the implantation space to be prepared into each of the two adjacent vertebral bodies from said trailing face and through said leading face of said milling block; and a bone cutting device for removing at least a portion of bone from the two endplates adjacent the disc space, said bone cutting device being configured to access at least one of the endplates of the adjacent vertebral bodies through said access aperture, said bone cutting device operating in cooperation with and at least in part through said access aperture of said milling block.

2. The apparatus of claim 1, wherein said access aperture is a slot.

3. The apparatus of claim 1, wherein said access aperture of said milling block is configured to permit motion by said bone cutting device transverse to the longitudinal axis of said bone cutting device over at least a portion of the width of said milling block through said access aperture.

4. The apparatus of claim 1, wherein said access aperture includes opposed substantially planar surfaces for guiding said bone cutting device therebetween provide the implantation space with at least one generally flat side.

5. The apparatus of claim 1, wherein the vertebral endplates each generally lie in a plane and said access aperture includes at least one flat portion for guiding said bone cutting device along a plane generally parallel to the plane of at least one of the vertebral endplates.

6. The apparatus of claim 1, wherein said access aperture in cooperation with said bone cutting device is configured to create the implantation space that is at least a portion of a parallelogram.

7. The apparatus of claim 6, wherein the parallelogram-shaped space is one of a square and a rectangle.

8. The apparatus of claim 1, wherein said access aperture has a width and includes an upper surface and a lower surface, said upper and lower surfaces being parallel to each other along a portion of the width of the access aperture.

9. The apparatus of claim 8, wherein said upper and lower surfaces of said access aperture are configured to permit said bone cutting device to remove a portion of only one vertebral body at a time.

10. The apparatus of claim 1, wherein the endplates of the adjacent vertebral bodies each generally lie in a plane and said access aperture has a height and a width larger than said height, said height being configured to slidably receive and guide said bone cutting device along a plane generally parallel to the plane of at least one of vertebral end plates.

11. The apparatus of claim 1, further comprising a second access aperture spaced apart from said access aperture.

12. The apparatus of claim 11, wherein said second access aperture is at least in part parallel to said access aperture.

13. The apparatus of claim 11, wherein the endplates of the adjacent vertebral bodies each generally lie in a plane and said access aperture has a portion for guiding said bone cutting device along a plane generally parallel to the plane of one of the adjacent vertebral endplates and said second access aperture has a portion for guiding said bone cutting device along a plane generally parallel to the plane of the other of said adjacent vertebral bodies.

14. The apparatus of claim 11, wherein said second access aperture is configured to guide said bone cutting device to form the implantation space that is at least a portion of a parallelogram along the width of the space.

15. The apparatus of claim 14, wherein the parallelogram-shaped space is one of a square and a rectangle.

16. The apparatus of claim 11, wherein said second access aperture is a slot.

17. The apparatus of claim 11, wherein said second access aperture is a track.

18. The apparatus of claim 1, wherein said milling block has a height less than its width.

19. The apparatus of claim 1, wherein said leading face is concave in at least one direction.

20. The apparatus of claim 1, wherein said milling block has a maximum depth less than its width.

21. The apparatus of claim 1, wherein said milling block has a depth greater than its maximum width.

22. The apparatus of claim 1, wherein said leading face of said milling block is adapted to conform to the shape of at least a portion of the anterior aspect of the adjacent vertebral bodies to be placed in contact with said milling block.

23. The apparatus of claim 1, wherein said leading face of said milling block is adapted to conform to the shape of the vertebral bodies along the posterior aspect of the lumbar spine on either side of the mid-sagittal axis of the adjacent vertebral bodies to be placed in contact with said milling block.

24. The apparatus of claim 1, wherein said bone cutting device cooperates with said access aperture and is configured to resect bone approximating the width of the implant to be inserted when said bone cutting device is inserted into said access aperture.

25. The apparatus of claim 24, wherein said bone cutting device is configured to resect bone from only one of the vertebral endplates at a time.

26. The apparatus of claim 1, wherein said bone cutting device is non-rotating.

27. The apparatus of claim 1, wherein said bone cutting device is one of a drill, burr, router bit, abrader, grinder, rasp, grater, saw, oscillating cutter, vibrating cutter, reciprocating cutter, orbital cutter, and rotating cutter.

28. The apparatus of claim 1, wherein said bone cutting device is a laser.

29. The apparatus of claim 1 in combination with at least one distractor for distracting and placing the adjacent vertebral bodies to be fused in selected spatial relationship to each other.

30. The apparatus of claim 29, wherein said at least one distractor includes at least a first disc penetrating extension extending beyond at least a portion of said leading face of said milling block when coupled to said milling block, said first disc penetrating extension adapted to extend into the disc space between the adjacent vertebral bodies when said milling block is placed against at least one of the adjacent vertebral bodies.

31. The apparatus of claim 30, wherein said first disc penetrating extension has a length that is less than the depth of the disc space into which said first disc penetrating extension is to be inserted.

32. The apparatus of claim 30, wherein said first disc penetrating extension is centrally placed in said leading face of said milling block.

33. The apparatus of claim 30, wherein said first disc penetrating extension is placed to one side in said leading face of said milling block.

34. The apparatus of claim 29, further comprising a second distractor having a second disc penetrating extension extending beyond at least a portion of said leading face of said milling block when coupled to said milling block, said second disc penetrating extension adapted to extend into the disc space between the adjacent vertebral bodies when said milling block is placed against at least one of the adjacent vertebral bodies.

35. The apparatus of claim 33, wherein said second disc penetrating extension is placed to a side in said leading face of said milling block opposite to the side with said first disc penetrating extension.

36. The apparatus of claim 30 in combination with a length adjuster for adjusting the length that said disc penetrating extension extends beyond at least a portion of said leading face of said milling block.

37. The apparatus of claim 30 in combination with a distractor holder for holding said distractor in a selected position relative to said milling block.

38. The apparatus of claim 37, wherein at least a portion of said disc penetrating extension extends through said access aperture and extends beyond at least a portion of said leading face and into the disc space when said milling block is placed against at least one of the adjacent vertebral bodies.

39. The apparatus of claim 37, wherein said distractor holder includes a coupler for coupling said distractor holder to said milling block.

40. The apparatus of claim 39 in combination with an aligner for aligning said distractor holder relative to said milling block.

41. The apparatus of claim 37, wherein said distractor holder includes a depth limiter for limiting the penetration depth of said disc penetrating extension of said distractor into the disc space.

42. The apparatus of claim 41, in combination with a lock for locking said disc penetrating extension at a selected penetration depth extending from said milling block.

43. The apparatus of claim 41 in combination with a calibrator for selecting the penetration depth of said disc penetrating extension.

44. The apparatus of claim 43, wherein said calibrator engages at least a portion of said distractor.

45. The apparatus of claim 1 in combination with at least one member for engaging said milling block to at least one of the adjacent vertebral bodies.

46. The apparatus of claim 45, wherein said engagement member includes a distractor for distracting and placing the adjacent vertebral bodies to be fused in selected spatial relationship to each other.

47. The apparatus of claim 45 wherein said engagement member is adapted to fixedly secure said milling block to at least one of the adjacent vertebral bodies.

48. The apparatus of claim 1 combination with a depth limiter for selecting and limiting the penetration depth of said bone cutting device into the disc space.

49. The apparatus of claim 48 in combination with a lock for locking said bone removal device at a selected penetration depth into the disc space.

50. The apparatus of claim 48 in combination with a calibrator for selecting the penetration depth of said bone cutting device into the disc space.

51. The apparatus of claim 50, wherein said calibrator engages at least a portion of said milling block.

52. The apparatus of claim 1 in combination with a guide located at least in part in said access aperture of said milling block for guiding and controlling the path of motion of an instrument associated with said guide.

53. The apparatus of claim 52, wherein said guide is configured to receive said bone cutting device.

54. The apparatus of claim 52, wherein said guide has a longitudinal axis and is in moveable relationship to said milling block for permitting motion transverse to said longitudinal axis by the instrument being guided by said guide.

55. The apparatus of claim 52, wherein said access aperture of said milling block has an axis passing through said access aperture and a transverse axis transverse to said axis of said milling block and said guide is oriented and adapted to travel along said transverse axis.

56. The apparatus of claim 52, wherein said guide is located at least in part within said access aperture of said milling block.

57. The apparatus of claim 52, wherein said milling block has an axis passing through said access aperture and said guide is in moveable relationship to said milling block along said axis of said access aperture.

58. The apparatus of claim 1 in combination with an aligner for aligning said milling block relative to the adjacent vertebral bodies.

59. The apparatus of claim 1 in combination with an aligner for aligning the adjacent vertebral bodies in a selected angular relationship to each other.

60. The apparatus of claim 1, wherein said milling block is configured to be coupled to at least one handle.

61. The apparatus of claim 1, wherein said milling block is separable into first and second portions, said first portion including said leading face for placement against the adjacent vertebral bodies and being configured to cooperatively engage said second portion.

62. The apparatus of claim 61, wherein said access aperture in said first portion is configured to permit the insertion of an implant therethrough and into the implantation space.

63. The apparatus of claim 61 in combination with at least one distractor for distracting and placing the adjacent vertebral bodies to be fused in selected spatial relationship to each other.

64. The apparatus of claim 63, wherein said at least one distractor includes at least a first disc penetrating extension extending beyond at least a portion of said leading face of said milling block when coupled to said milling block, said first disc penetrating extension adapted to extend into the disc space between the adjacent vertebral bodies when said milling block is placed against at least one of the adjacent vertebral bodies.

65. An apparatus adapted for use in spinal surgery for creating a space of selected shapes and dimensions at least in within and across the height of the disc space between two adjacent vertebral bodies of the spine, each of the two adjacent vertebral bodies having an endplate adjacent to the disc space, said apparatus comprising:

a milling block configured at least in part for placement across the height of the disc space and against at least a portion of the outer surfaces of the adjacent vertebral bodies, said milling block having a leading face for placement against the vertebral bodies and an opposite trailing face, said milling block having a width and an access aperture configured for providing access for the width of the space to be prepared to at least one of the adjacent vertebral bodies from said trailing face and through said leading face of said milling block; and a bone cutting device for removing at least a portion of bone from at least one of the endplates adjacent the disc space, said bone cutting device being configured to access at least one of the adjacent vertebral bodies proximate the disc through said access aperture, said access aperture of said milling block being adapted to permit a generally flat cut of bone along the width of the space being created through said access aperture, said bone cutting device operating in cooperation with and at least in part through said milling block to make a generally flat cut of bone along the width of the space being created in at least one of the adjacent vertebral bodies.

66. The apparatus of claim 65, wherein said access aperture is a slot.

67. The apparatus of claim 65, wherein said access aperture of said milling block is configured to permit motion by said bone cutting device transverse to the longitudinal axis of said bone cutting device over at least a portion of the width of said milling block through said access aperture.

68. The apparatus of claim 65, wherein said access aperture includes opposed substantially planar surfaces for guiding said bone cutting device therebetween to provide the implantation space with at least one generally flat side.

69. The apparatus of claim 65, wherein the vertebral endplates each generally lie in a plane and said access aperture includes at least one flat portion for guiding said bone cutting device along a plane generally parallel to the plane of at least one of the vertebral endplates.

70. The apparatus of claim 65, wherein said access aperture in cooperation with said bone cutting device is configured to create the implantation space that is at least a portion of a parallelogram.

71. The apparatus of claim 70, wherein the parallelogram-shaped space is one of a square and a rectangle.

72. The apparatus of claim 65, wherein said access aperture has a width and includes an upper surface and a lower surface, said upper and lower surfaces being parallel to each other along a portion of the width of the access aperture.

73. The apparatus of claim 72, wherein said upper and lower surfaces of said access aperture are configured to permit said bone cutting device to remove a portion of only one vertebral body at a time.

74. The apparatus of claim 65, wherein the endplates of the adjacent vertebral bodies each generally lie in a plane and said access aperture has a height and a width larger than said height, said height being configured to slidably receive and guide said bone cutting device along a plane generally parallel to the plane of at least one of the vertebral endplates.

75. The apparatus of claim 65, further comprising a second access aperture spaced apart from said access aperture.

76. The apparatus of claim 75, wherein said second access aperture is at least in part parallel to said access aperture.

77. The apparatus of claim 75, wherein the endplates of the adjacent vertebral bodies each generally lie in a plane and said access aperture has a portion for guiding said bone cutting device along a plane generally parallel to the plane of one of the adjacent vertebral endplates and said second access aperture has a portion for guiding said bone cutting device along a plane generally parallel to the plane of the other of said adjacent vertebral bodies.

78. The apparatus of claim 75, wherein said second access aperture is configured to guide said bone cutting device to form the implantation space that is at least a portion of a parallelogram along the width of the space.

79. The apparatus of claim 78, wherein the parallelogram-shaped space is one of a square and a rectangle.

80. The apparatus of claim 75, wherein said second access aperture is a slot.

81. The apparatus of claim 75, wherein said second access aperture is a track.

82. The apparatus of claim 65, wherein said bone cutting device cooperates with said access aperture and is configured to resect bone approximating the width of the implant to be inserted when said bone cutting device is inserted into said access aperture.

83. The apparatus of claim 82, wherein said bone cutting device is configured to resect bone from only one of the vertebral endplates at a time.

84. The apparatus of claim 65 wherein said bone cutting device is non-rotating.

85. The apparatus of claim 65, wherein said bone cutting device is one of a drill, burr, router bit, abrader, grinder, rasp, grater, saw, oscillating cutter, vibrating cutter, reciprocating cutter, orbital cutter, and rotating cutter.

86. The apparatus of claim 65, wherein said bone cutting device is a laser.

87. The apparatus of claim 65 in combination with at least one distractor for distracting and placing the adjacent vertebral bodies to be fused in selected spatial relationship to each other.

88. The apparatus of claim 65 in combination with a guide located at least in part in said access aperture of said milling block for guiding and controlling the path of motion of instrument associated with said guide.

89. The apparatus of claim 88, wherein said guide is configured to receive said bone cutting device.

90. The apparatus of claim 88, wherein said guide has a longitudinal axis and is in moveable relationship to said milling block for permitting motion transverse to said longitudinal axis by the instrument being guided by said guide.

91. The apparatus of claim 65, wherein said milling block is separable into first and second portions, said first portion including said leading face for placement against the adjacent vertebral bodies and being configured to cooperatively engage said second portion.

92. An apparatus used in spinal surgery for creating a space of selected shapes and dimensions across the disc space between two adjacent vertebral bodies of the spine, each of the two adjacent vertebral bodies having an endplate adjacent to the disc space, said apparatus comprising:

a milling block configured at least in part for placement across the disc space and against the outer surface of the adjacent vertebral bodies, said milling block having a front face for placement against the vertebral bodies and an opposite rear face, said milling block having a width and at least two access apertures each being configured to provide access to the adjacent vertebral bodies from said trailing face and through said leading face of said milling block, each of said access apertures being configured to permit a bone cutting device to access the endplates of the adjacent vertebral bodies to create an implantation space across the disc space and into the adjacent vertebral bodies.

93. The apparatus of claim 92, wherein at least one of said access apertures is a slot.

94. The apparatus of claim 92, wherein at least one of said access apertures of said milling block is configured to permit motion by said bone cutting device transverse to the longitudinal axis of said bone cutting device over at least a portion of the width of said milling block through said access aperture.

95. The apparatus of claim 92, wherein at least one of said access apertures includes opposed substantially planar surfaces for guiding said bone cutting device therebetween to provide the implantation space with at least one generally flat side.

96. The apparatus of claim 92, wherein the vertebral endplates each generally lie in a plane and at least one of said access apertures includes at least one flat portion for guiding said bone cutting device along a plane generally parallel to the plane of at least one of the vertebral end plates.

97. The apparatus of claim 92, wherein said access apertures in cooperation with said bone cutting device are configured to create the implantation space that is at least a portion of a parallelogram.

98. The apparatus of claim 97, wherein the parallelogram-shaped space is one of a square and a rectangle.

99. The apparatus of claim 92, wherein at least one of said access apertures has a width and includes an upper surface and a lower surface, said upper and lower surfaces being parallel to each other along a portion of the width of the access aperture.

100. The apparatus of claim 99, wherein said upper and lower surfaces of said access aperture are configured to permit said bone cutting device to remove a portion of only one vertebral body at a time.

101. The apparatus of claim 92, wherein the endplates of the adjacent vertebral bodies each generally lie in a plane and at least one of said access apertures has a height and a width larger than said height, said height being configured to slidably receive and guide said bone cutting device along a plane generally parallel to the plane of at least one of the vertebral endplates.

102. The apparatus of claim 92, wherein at least one of said second access apertures is curved.

103. The apparatus of claim 92, wherein at least one of said second access apertures is a track.

104. The apparatus of claim 92 wherein said bone cutting device cooperates with at least one of said access apertures and is configured to resect bone approximating the width of the implant to be inserted when said bone cutting device is inserted into said access aperture.

105. The apparatus of claim 92 wherein said bone cutting device is non-rotating.

106. The apparatus of claim 92, wherein said bone cutting device is one of a drill, burr, router bit, abrader, grinder, rasp, grater, saw, oscillating cutter, vibrating cutter, reciprocating cutter, orbital cutter, and rotating cutter.

107. The apparatus of claim 92, wherein said bone cutting device is a laser.

108. The apparatus of claim 92 combination with at least one distractor for distracting and placing the adjacent vertebral bodies to be fused in selected spatial relationship to each other.

109. The apparatus of claim 92 in combination with at least one guide located at least in part in one of said access apertures of said milling block for guiding and controlling the path of motion of an instrument associated with said guide.

110. The apparatus of claim 109, wherein said guide is configured to receive said bone cutting device.

111. The apparatus of claim 109, wherein said guide has a longitudinal axis and is in moveable relationship to said milling block for permitting motion transverse to said longitudinal axis by the instrument being guided by said guide.

112. The apparatus of claim 92, wherein said milling block is separable into first and second portions, said first portion including said leading face for placement against the adjacent vertebral bodies and being configured to cooperatively engage said second portion.

113. A method for creating a space of selected shape across a disc space between adjacent vertebral bodies of the spine, each of the adjacent vertebral bodies having an endplate adjacent to the disc space, the method comprising the steps of:

placing a milling block having at least one non-circular access aperture across the disc space and in contact with the outer surface of the adjacent vertebral bodies;

removing bone through the non-circular access aperture from one of the adjacent vertebral bodies with a bone cutting device; and then removing bone from the other one of the adjacent vertebral bodies with a bone cutting device.

114. The method of claim 113, wherein the steps of removing bone are performed through the same non-circular access aperture.

115. The method of claim 113, wherein the second step of removing bone is performed through a second non-circular access aperture.

116. The method of claim 115, further comprising the step of moving the bone removal device transversely across a width of the disc space.

117. The method of claim 116, further comprising the step of moving the bone removal device through the non-circular aperture along a plane generally parallel to at least one of the vertebral endplates.

118. The method of claim 116, wherein the bone removing steps include removing bone from the adjacent vertebral bodies with a non-rotating bone cutting device.

119. The method of claim 116, wherein the first step of removing bone from one of the adjacent vertebral bodies is through a first access aperture; and the second step of removing bone from the other one of the adjacent vertebral bodies is through a second access aperture.

* * * * *

UNITED STATES PATENT AND TRADEMARK OFFICE
CERTIFICATE OF CORRECTION

PATENT NO. : 6,440,139 B2
DATED : August 27, 2002
INVENTOR(S) : Gary K. Michelson It is certified that error appears in the above-identified patent and that said Letters Patent is hereby corrected as shown below:

Column 24,
Line 35, after "therebetween" insert -- to --.

Column 29,
Line 28, before "instrument" insert -- an --.

Column 30,
Line 34, delete "second".
Line 36, delete "second".

Signed and Sealed this

Tenth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO. : 6,440,139 B2
DATED : August 27, 2004
INVENTOR(S) : Gary K. Michelson It is certified that error appears in the above-identified patent and that said Letters Patent is hereby corrected as shown below:

Column 24,
Line 36, after "therebetween" insert -- to --.

Column 29,
Line 28, before "instrument" insert -- an --.

Column 30,
Line 32, delete "second".
Line 34, delete "second".

This certificate supersedes Certificate of Correction issued December 10, 2002.

Signed and Sealed this

Ninth Day of November, 2004

JON W. DUDAS
*Director of the United States Patent and Trademark Office*